United States Patent
Rodriguez et al.

(10) Patent No.: US 11,246,604 B2
(45) Date of Patent: Feb. 15, 2022

(54) REAMING ASSEMBLIES FOR PREPARATION OF SURGICAL SITES

(71) Applicant: Arthrex, Inc., Naples, FL (US)

(72) Inventors: Alexander Emmanuel Rodriguez, Weston, FL (US); Rudraksh Khosla, Naples, FL (US); Tyler Clevett, Bonita Springs, CT (US); Gregory Guederian, Naples, FL (US); John David Paterson, Naples, FL (US)

(73) Assignee: ARTHREX, INC., Naples, FL (US)

( * ) Notice: Subject to any disclaimer, the term of this patent is extended or adjusted under 35 U.S.C. 154(b) by 54 days.

(21) Appl. No.: 16/590,754

(22) Filed: Oct. 2, 2019

(65) Prior Publication Data

US 2021/0100562 A1 Apr. 8, 2021

(51) Int. Cl.
*A61B 17/16* (2006.01)

(52) U.S. Cl.
CPC ...... *A61B 17/1615* (2013.01); *A61B 17/1631* (2013.01); *A61B 17/1662* (2013.01)

(58) Field of Classification Search
CPC ............ A61B 17/1615; A61B 17/1631; A61B 17/1666; A61B 17/1684; A61B 17/1662
See application file for complete search history.

(56) References Cited

U.S. PATENT DOCUMENTS

| | | |
|---|---|---|
| 5,020,281 A | 6/1991 | Neff |
| 6,245,074 B1 | 6/2001 | Allard et al. |
| 6,884,246 B1 | 4/2005 | Sonnabend et al. |
| 7,326,215 B2 | 2/2008 | Myers et al. |
| 7,503,921 B2 | 3/2009 | Berthusen et al. |
| 7,758,581 B2 | 7/2010 | Chervilz et al. |
| 9,358,029 B2 | 6/2016 | Sikora et al. |
| 9,408,613 B2 | 8/2016 | Kehres et al. |
| 9,737,313 B1 | 8/2017 | Sohn et al. |
| 9,839,438 B2 | 12/2017 | Eash |
| 10,028,838 B2 | 7/2018 | Hodorek et al. |
| 2004/0153080 A1 | 8/2004 | Dong et al. |
| 2004/0267267 A1 | 12/2004 | Daniels et al. |
| 2005/0159751 A1 | 7/2005 | Berthusen et al. |
| 2006/0142865 A1 | 6/2006 | Hyde, Jr. |
| 2006/0217728 A1 | 9/2006 | Chervilz et al. |
| 2008/0009874 A1 | 1/2008 | Meridew et al. |
| 2010/0076442 A1 | 3/2010 | Xie et al. |
| 2011/0098710 A1 | 4/2011 | Spratt et al. |

(Continued)

FOREIGN PATENT DOCUMENTS

| | | |
|---|---|---|
| CN | 103767759 | 5/2014 |
| CN | 104605913 | 5/2015 |

(Continued)

OTHER PUBLICATIONS

International Search Report and Written Opinion for International Application No. PCT/US2020/053906 completed Jan. 15, 2021.

*Primary Examiner* — Matthew J Lawson
*Assistant Examiner* — Lisa Nguyen
(74) *Attorney, Agent, or Firm* — Carlson, Gaskey & Olds, P.C.

(57) ABSTRACT

This disclosure relates to reaming assemblies and methods for repairing bone defects. The reaming assemblies disclosed herein may be utilized for removing bone prior to positioning a graft and/or implant at a surgical site.

17 Claims, 23 Drawing Sheets

(56) References Cited

U.S. PATENT DOCUMENTS

| | | | |
|---|---|---|---|
| 2013/0331841 A1 | 12/2013 | Roger et al. | |
| 2014/0012389 A1 | 1/2014 | Ek | |
| 2015/0119891 A1 | 4/2015 | Goldberg et al. | |
| 2015/0190151 A1 | 7/2015 | Budhabhatti et al. | |
| 2015/0374502 A1* | 12/2015 | Hodorek | A61F 2/4081 623/19.11 |
| 2016/0045207 A1 | 2/2016 | Kovacs et al. | |
| 2016/0345987 A1 | 12/2016 | Guilloux et al. | |
| 2018/0008293 A1 | 1/2018 | Kovacs et al. | |
| 2018/0200068 A1 | 7/2018 | Goldberg et al. | |
| 2019/0015118 A1 | 1/2019 | Neichel et al. | |

FOREIGN PATENT DOCUMENTS

| | | |
|---|---|---|
| DE | 102008053566 | 6/2009 |
| EP | 1410763 | 4/2004 |
| EP | 2962650 | 1/2016 |
| GB | 2281577 | 3/1995 |
| WO | 2015106136 | 7/2015 |

* cited by examiner

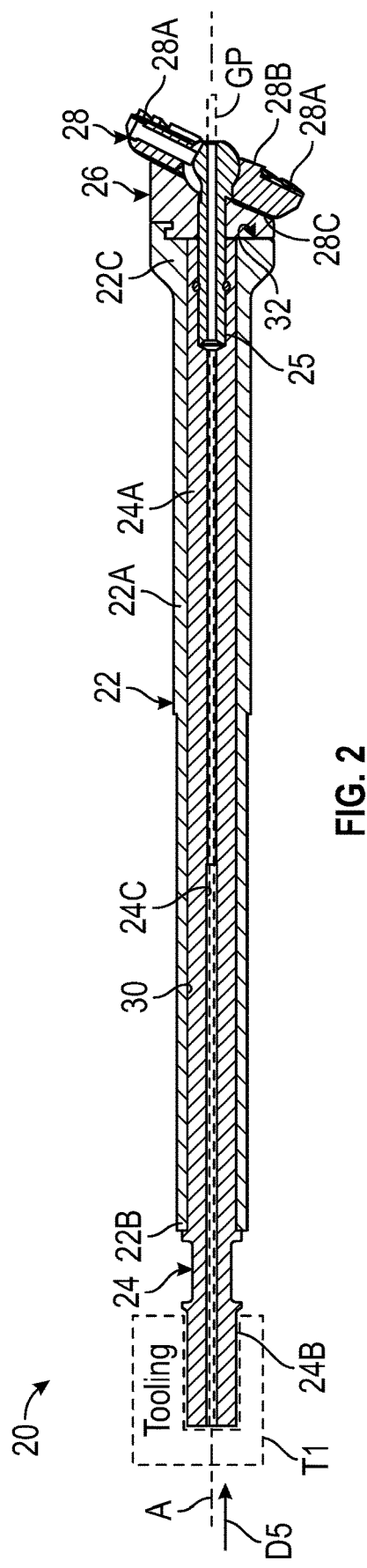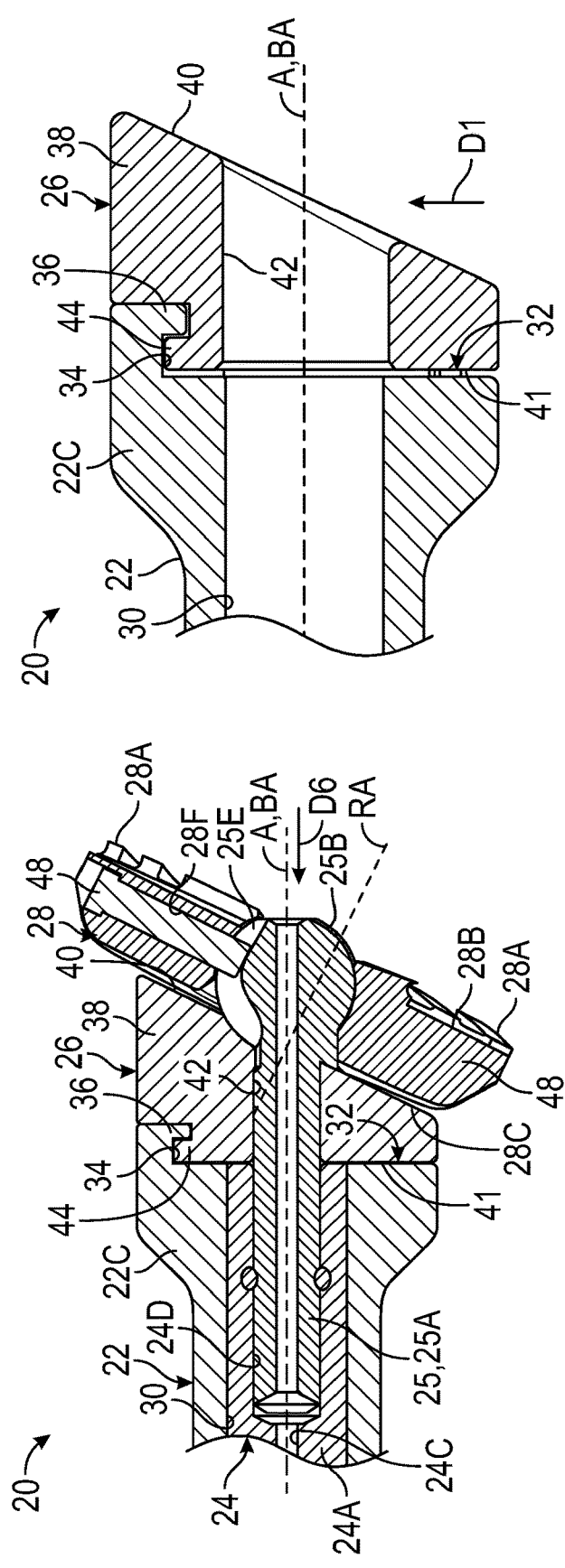

REAMING ASSEMBLIES FOR PREPARATION OF SURGICAL SITES

BACKGROUND

This disclosure relates to surgical devices and methods for repairing bone defects.

Many bones of the human musculoskeletal system include articular surfaces. The articular surfaces articulate relative to other bones to facilitate different types and degrees of joint movement. The articular surfaces can erode (i.e., experience bone loss) over time due to repeated use or wear or can fracture as a result of a traumatic impact. These types of bone defects can cause joint instability and pain.

Bone deficiencies may occur along the articular surfaces of the glenoid bone. Some techniques utilize a bone graft and/or implant to a fill defect in the glenoid bone. A reamer may be utilized to form a recess in the bone dimensioned to receive the bone graft or implant.

SUMMARY

This disclosure relates to surgical devices and methods. The surgical device may be used during methods for repairing bone defects. The surgical devices described herein may be utilized to form a recess or otherwise shape a surface at a surgical site.

A reaming assembly for preparation of a surgical site according to an embodiment of the present disclosure includes, inter alia, a housing defining a passageway that extends along a longitudinal axis, a rotatable drive shaft at least partially received in the passageway, a reaming head pivotably coupled to a reaming carrier, the reaming carrier operably coupled to the drive shaft, the reaming head including a plurality of teeth rotatable about a reaming axis, and at least one control block including a block body having a control surface and a through bore extending from the control surface along a block axis. The at least one control block is dimensioned to slidably engage the housing along an interface to secure the at least one control block such that the control surface faces away from a distal end portion of the housing, the through bore is dimensioned to at least partially receive the reaming carrier, the control surface is non-orthogonal relative to the block axis such that a reaming angle is defined between the longitudinal axis and the reaming axis, and the reaming head is rotatable along the control surface to remove bone.

A reaming assembly for preparation of a surgical site according to an embodiment of the present disclosure includes, inter alia, a housing defining a passageway that extends along a longitudinal axis, a rotatable drive shaft at least partially received in the passageway, a reaming head operably coupled to the drive shaft, the reaming head including a plurality of teeth rotatable about a reaming axis, and a head assembly coupled to the housing, the head assembly including a head plate and a drive member, the head plate having a control flange and a plate body having a control surface, and the control flange extending from the plate body and engaging the drive member. The reaming head is rotatable along the control surface to remove bone, and the control flange adjusts an orientation of the control surface relative to the longitudinal axis in response to rotation of the drive member.

A method of use for a reaming assembly to prepare a surgical site in bone according to an embodiment of the present disclosure includes, inter alia, slidably engaging a head assembly along an interface to secure the head assembly to a distal end portion of a housing, wherein the housing defines a passageway that extends along a longitudinal axis, the head assembly defines a through bore extending from a control surface, inserting a reaming carrier into the passageway and the through bore, wherein the reaming carrier is pivotably coupled to a reaming head along the longitudinal axis such that the control surface faces away from the distal end portion of the housing at a non-orthogonal angle relative to the longitudinal axis, and rotating the reaming head along the control surface to remove bone in response to rotating a drive shaft operably coupled to the reaming carrier.

BRIEF DESCRIPTION OF THE DRAWINGS

FIG. 2 illustrates a sectional view of the reaming assembly of FIG. 1.

FIG. 3 illustrates selected portions of the reaming assembly of FIG. 2.

FIG. 4 illustrates a head assembly coupled to a housing of the reaming assembly of FIG. 3.

DETAILED DESCRIPTION

Figure 1:
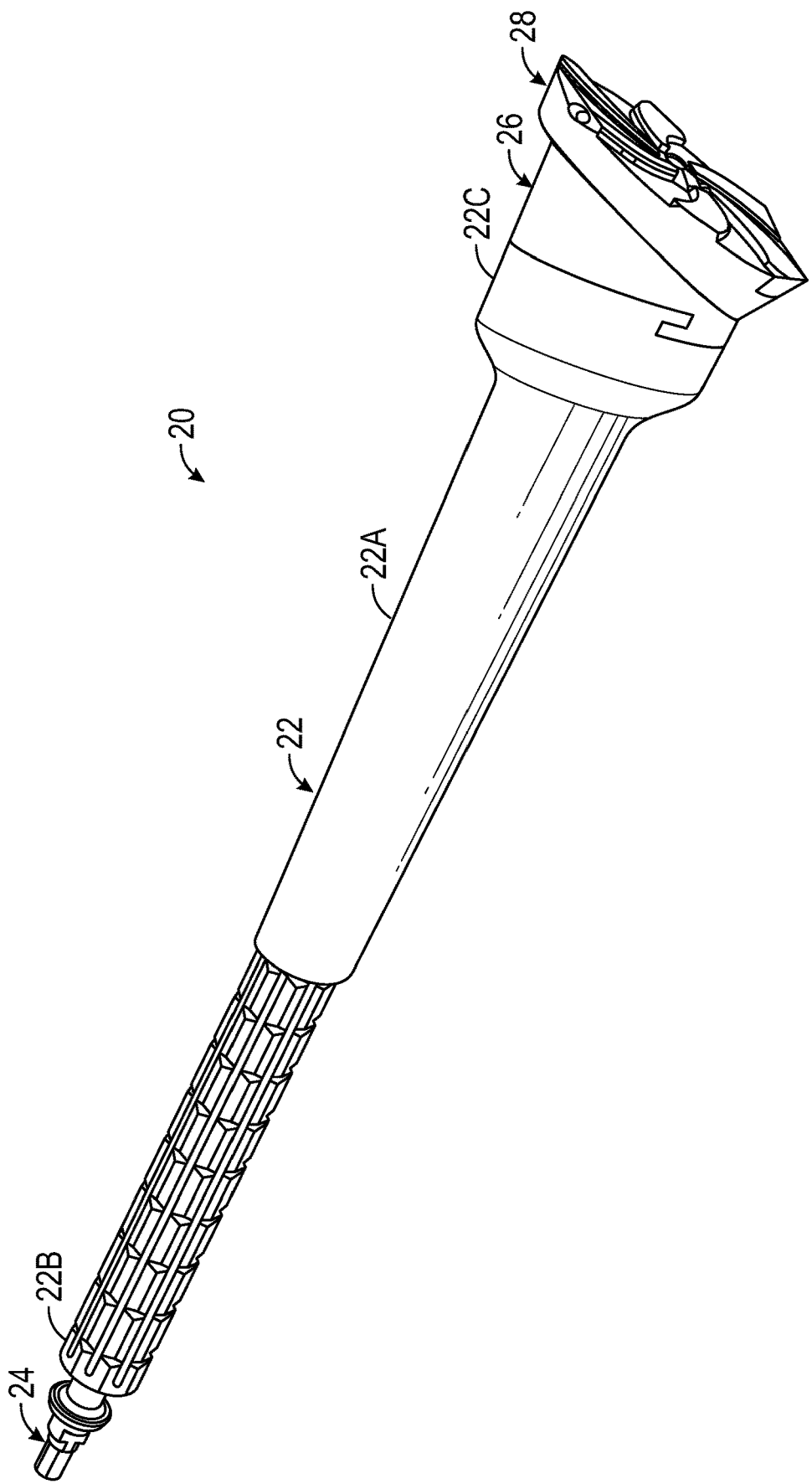
FIG. 1 illustrates a perspective view of an exemplary reaming assembly for preparing a surgical site.
Figure 5:
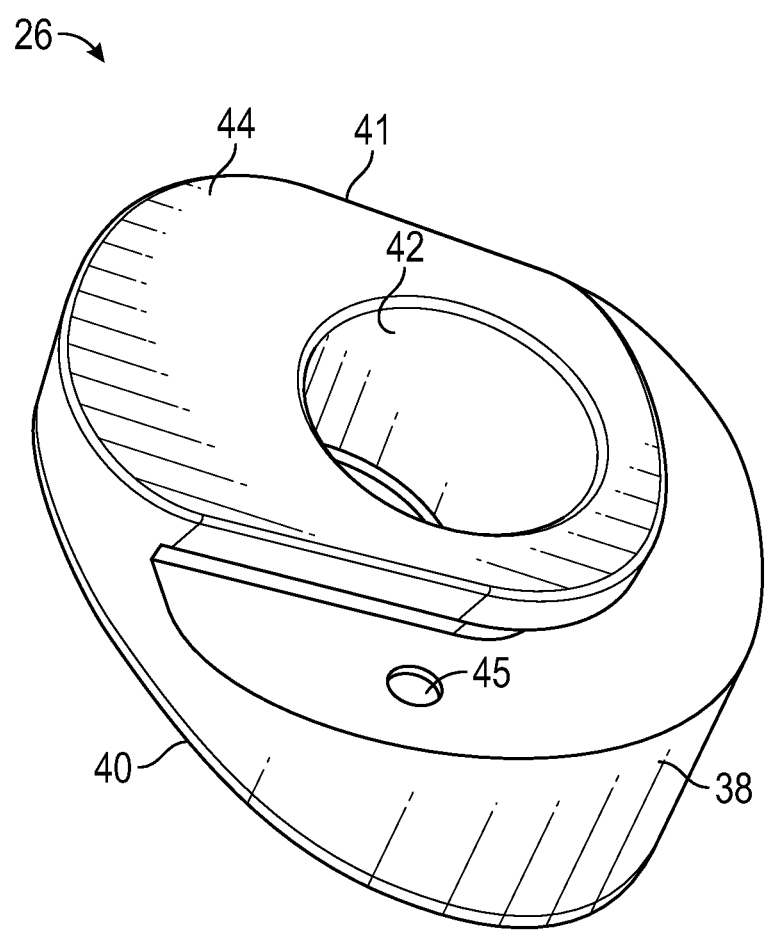
FIG. 5 illustrates an isolated perspective view of the head assembly of FIG. 4.

This disclosure relates to surgical devices and methods for repairing bone defects. The devices described herein may be capable of dimensioning or otherwise preparing a defect surface at a surgical site, including reaming bone or other tissue.

A reaming assembly for preparation of a surgical site according to an exemplary aspect of the present disclosure includes, inter alia, a housing defining a passageway that extends along a longitudinal axis, a rotatable drive shaft at least partially received in the passageway, a reaming head pivotably coupled to a reaming carrier, the reaming carrier operably coupled to the drive shaft, the reaming head including a plurality of teeth rotatable about a reaming axis, and at least one control block including a block body having a control surface and a through bore extending from the control surface along a block axis. The at least one control block is dimensioned to slidably engage the housing along an interface to secure the at least one control block such that the control surface faces away from a distal end portion of the housing, the through bore is dimensioned to at least partially receive the reaming carrier, the control surface is non-orthogonal relative to the block axis such that a reaming angle is defined between the longitudinal axis and the reaming axis, and the reaming head is rotatable along the control surface to remove bone.

In a further embodiment, the at least one control block includes first and second control blocks dimensioned such that the reaming angle of the first control block differs from the reaming angle of the second control block.

In a further embodiment, the at least one control block is dimensioned to space apart the reaming head and the housing in an installed position.

In a further embodiment, the at least one control block includes a mounting flange extending outwardly from the block body, and the distal end portion of the housing defines a slot dimensioned to slidably receive the mounting flange along the interface to limit axial movement of the at least one control block relative to the longitudinal axis.

In a further embodiment, the mounting flange is dimensioned such that the block body translates through a projection of the longitudinal axis in response to moving the mounting flange along the interface.

In a further embodiment, the drive shaft is a cannulated drive shaft including an inner bore dimensioned to receive a guide pin.

In a further embodiment, at least one locking member includes an engagement pin moveable between a retracted position and an extended position, and the engagement pin extends across the interface to oppose movement of the at least one control block relative to the housing along the interface in the extended position.

A reaming assembly for preparation of a surgical site according to an exemplary aspect of the present disclosure includes, inter alia, a housing defining a passageway that extends along a longitudinal axis, a rotatable drive shaft at least partially received in the passageway, a reaming head operably coupled to the drive shaft, the reaming head including a plurality of teeth rotatable about a reaming axis, and a head assembly coupled to the housing, the head assembly including a head plate and a drive member, the head plate having a control flange and a plate body having a control surface, and the control flange extending from the plate body and engaging the drive member. The reaming head is rotatable along the control surface to remove bone, and the control flange adjusts an orientation of the control surface relative to the longitudinal axis in response to rotation of the drive member.

In a further embodiment, the reaming head is pivotably attached to a reaming carrier, and the reaming carrier interconnects the reaming head and the drive shaft.

In a further embodiment, the drive shaft is coupled to the reaming carrier at a position within the passageway, the drive shaft extends outwardly from a proximal end portion of the housing, and the reaming carrier extends through an opening defined in the control surface.

In a further embodiment, the reaming carrier includes an elongated drive portion extending from a head portion, the drive portion coupled to drive shaft, the head portion is pivotably attached to the reaming head, and the head portion includes a plurality of protrusions dimensioned to mesh with the plurality of teeth.

In a further embodiment, the drive shaft is a cannulated drive shaft including an inner bore dimensioned to at least partially receive a guide pin.

In a further embodiment, the drive member includes a worm drive that meshes with a plurality of engagement teeth along the control flange.

In a further embodiment, the worm drive is rotatable about a drive axis that is transverse to the longitudinal axis.

In a further embodiment, the reaming head is pivotably attached to a reaming carrier, the reaming carrier interconnects the reaming head and the drive shaft, the reaming carrier extends through an opening defined in the control surface, the head plate is pivotable relative to the longitudinal axis to set a reaming angle of the reaming head in response to translation of the plurality of engagement teeth along the worm drive, and the reaming carrier is straight when the head plate is positioned at the maximum angle.

In a further embodiment, the head plate is pivotably attached to a distal end portion of the housing.

In a further embodiment, the control flange defines an arcuate groove dimensioned to receive one or more support pins fixedly attached to the distal end portion of the housing.

In a further embodiment, the head assembly includes a support releasably secured to a distal end portion of the housing at an interface, and the control flange is pivotably attached to the support.

In a further embodiment, the drive member includes a worm drive that meshes with a plurality of engagement teeth along the control flange, the support defines a recess that at least partially receives the control flange, and the worm drive is at least partially received in the support.

In a further embodiment, the worm drive extends along a worm shaft, the worm shaft includes a head portion dimensioned to engage tooling to rotate the worm shaft about a drive axis, and the distal end portion of the housing includes an access flange dimensioned to at least partially block access to the head portion when the support is secured to the housing.

In a further embodiment, the support slidably engages the distal end portion of the housing along the interface to limit axial movement of the support relative to the longitudinal axis.

In a further embodiment, at least one locking member includes an engagement pin moveable between a retracted position and an extended position, and wherein the engagement pin extends across the interface to oppose movement of the support relative to the distal end portion of the housing along the interface in the extended position.

A method of use for a reaming assembly to prepare a surgical site in bone according to an exemplary aspect of the present disclosure includes, inter alia, slidably engaging a head assembly along an interface to secure the head assembly to a distal end portion of a housing, wherein the housing defines a passageway that extends along a longitudinal axis, the head assembly defines a through bore extending from a control surface, inserting a reaming carrier into the passageway and the through bore, wherein the reaming carrier is pivotably coupled to a reaming head along the longitudinal axis such that the control surface faces away from the distal end portion of the housing at a non-orthogonal angle relative to the longitudinal axis, and rotating the reaming head along the control surface to remove bone in response to rotating a drive shaft operably coupled to the reaming carrier.

In a further embodiment, the step of rotating the reaming head includes removing the bone from a glenoid of a patient.

In a further embodiment, the method includes coupling the reaming carrier and a drive shaft in the passageway, the drive shaft being a cannulated drive shaft including an inner bore, positioning a guide pin at least partially in the inner bore, and rotating the reaming head about the guide pin to remove the bone.

In a further embodiment, the step of slidably engaging the head assembly includes moving the head assembly through a projection of the longitudinal axis.

In a further embodiment, the head assembly includes a support, a head plate and a drive member, the support defines the interface, the head plate has a plate body including the control surface and a control flange extending from the plate body to engage the drive member, and the control flange is pivotably attached to the support. The method includes adjusting a reaming angle of the reaming head in response to rotation of the drive member.

In a further embodiment, the drive member includes a worm drive that meshes with a plurality of engagement teeth along the control flange, and the step of adjusting the reaming angle includes rotating the worm drive about a drive axis to cause the plurality of engagement teeth to translate along the worm drive.

FIGS. 1-17 illustrate an exemplary reaming assembly 20 that can be utilized for various surgical procedures, such as for preparation of a surgical site. For example, the reaming assembly 20 may be utilized in a shoulder reconstruction to remove bone along an articulating surface of a glenoid or humeral head. The bone may be removed from a defect in the articulating surface.

Referring to FIGS. 1-2, the reaming assembly 20 includes a housing 22, a rotatable drive shaft 24, a head assembly or control block 26 releasably secured to the housing 22, and a reaming head 28 coupled to the drive shaft 24. The housing 22 includes a generally cylindrical shaped, elongated body 22A that extends between a proximal end portion 22B and a distal end portion 22C.

Referring to FIGS. 2-3, with continuing reference to FIG. 1, the body 22A defines a passageway 30 that extends along a longitudinal axis A between the proximal and distal end portions 22B, 22C. The drive shaft 24 is at least partially received in the passageway 30. The drive shaft 24 includes an elongated shaft portion 24A extending from an interface portion 24B (FIG. 2). The shaft portion 24A is coupled to an elongated reaming carrier 25 at a position within the passageway 30. The shaft portion 24A and the reaming carrier 25 can establish a socket connection, for example. In other embodiments, the shaft portion 24A and reaming carrier 25 are integrally formed as a single component. The reaming carrier 25 interconnects the reaming head 28 and the drive shaft 24. The shaft portion 24A is dimensioned to extend outwardly from the proximal end portion 22B of the housing 22 (see FIG. 2), and the reaming carrier 25 is dimensioned to extend outwardly of the distal end portion 22C of the housing. The drive shaft 24 and reaming carrier 25 can be substantially rigid or can be flexible. The interface portion 24B of the drive shaft 24 can be coupled to tooling T1 (shown in dashed lines in FIG. 2 for illustrative purposes) to rotate the drive shaft 24 about the longitudinal axis A.

The reaming head 28 is pivotably coupled to the reaming carrier 25 such that the longitudinal axis A intersects the reaming head 28. The reaming head 28 includes a plurality of teeth 28A distributed along a reaming surface 28B opposed to an engagement surface 28C. The teeth 28A of the reaming head 28 are rotatable in a direction R1 (FIG. 15) about a reaming axis RA to remove bone or other tissue from a surgical site.

In the illustrated embodiment of FIGS. 2-3, the drive shaft 24 is a cannulated drive shaft including an inner bore 24C. The inner bore 24C is dimensioned to receive an elongated guide pin GP (shown in dashed lines for illustrative purposes). The guide pin GP can be secured in a surgical site. The reaming assembly 20 can be translated along the guide pin GP to engage surfaces of the surgical site at a selected location and/or orientation.

Referring to FIGS. 3-4, with continuing reference to FIGS. 1-2, the control block 26 is dimensioned to set an orientation of the reaming head 28 relative to the longitudinal axis A. The control block 26 is a modular component dimensioned to slidably engage the distal end portion 22C of the housing 22 along an interface 32 to secure the control block 26 to the housing 22. The control block 26 can be dimensioned to space apart the reaming head 28 and housing 22 in an installed position, as illustrated by FIG. 3.

Figure 12:
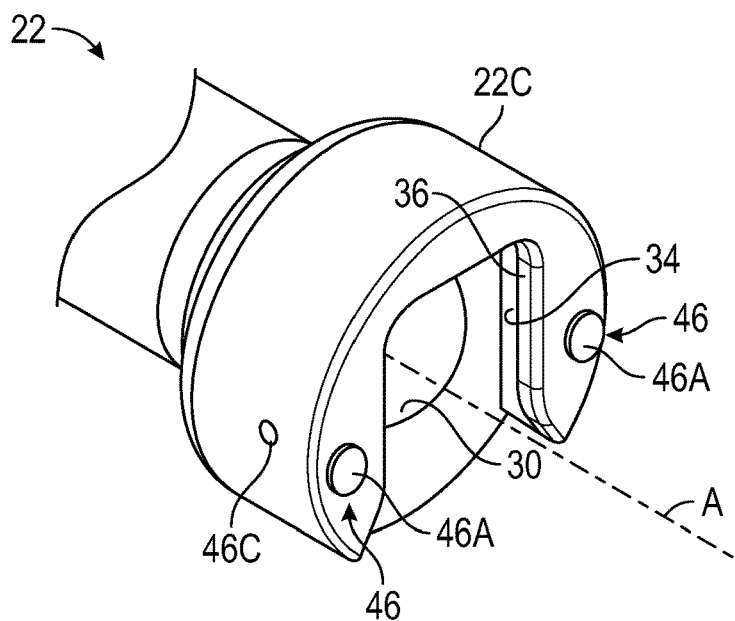
FIG. 12 illustrates a perspective view of selected portions of the housing and locking members of FIG. 11.
Figure 13:
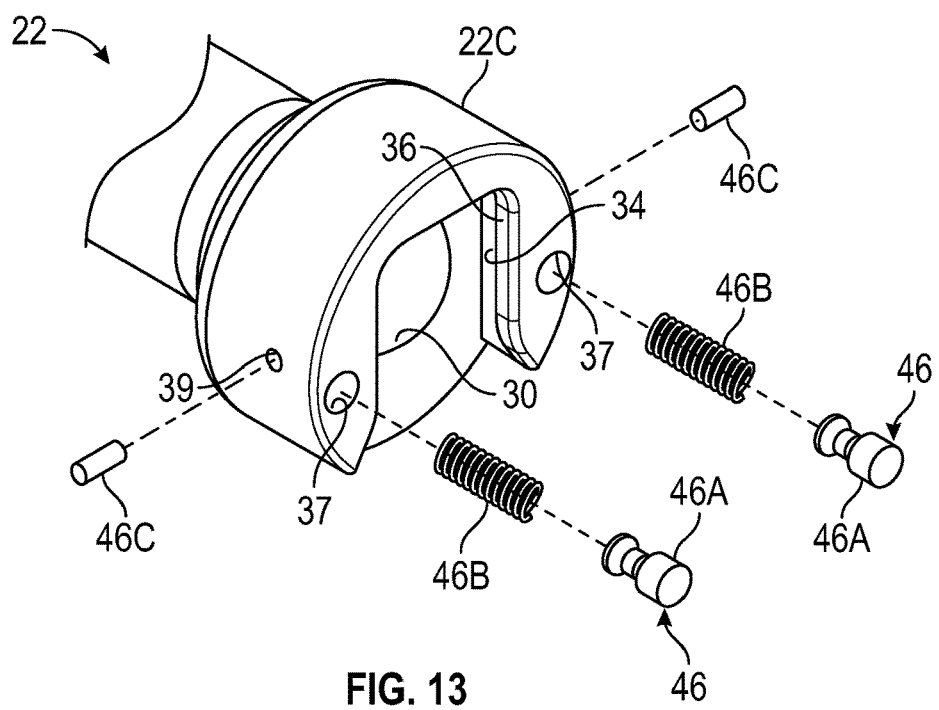
FIG. 13 illustrates an exploded view of the housing of FIG. 12.

The distal end portion 22C of the housing 22 defines a retention slot 34 that extends inwardly from a retention flange 36. The flange 36 can have a generally C-shaped geometry, as illustrated in FIGS. 12-13. The passageway 30 extends inwardly from the slot 34.

Figure 6:
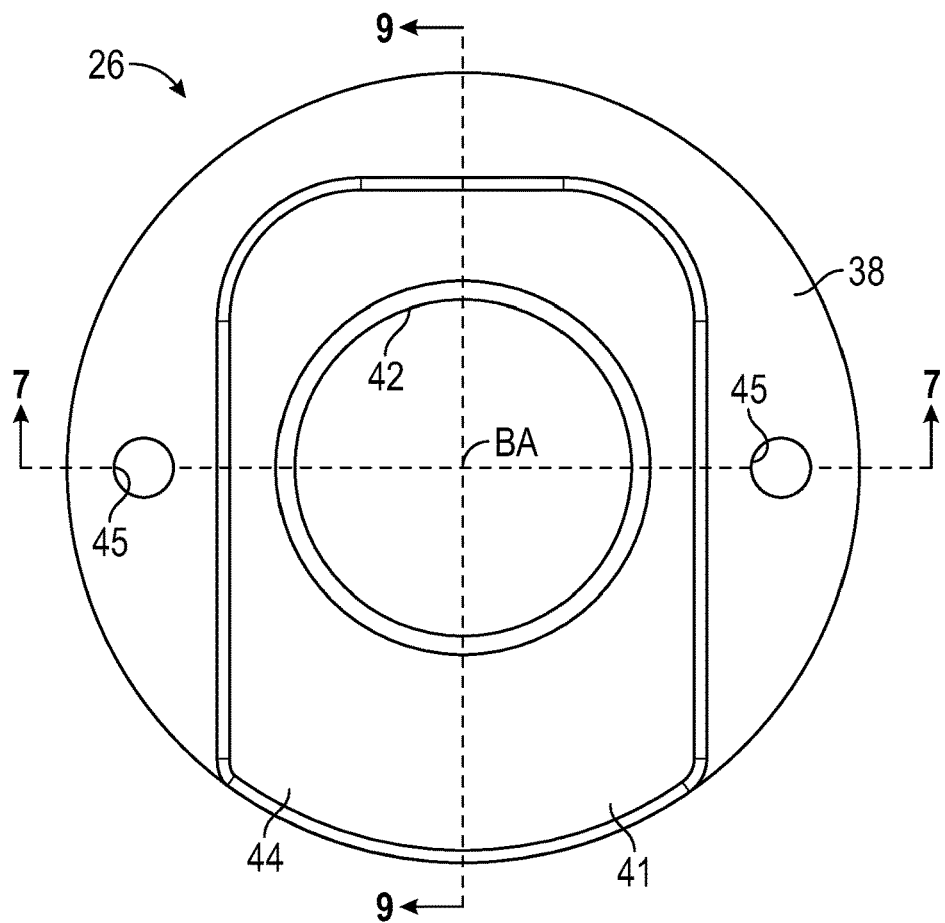
FIG. 6 illustrates a plan view of the head assembly of FIG. 5.
Figure 8:
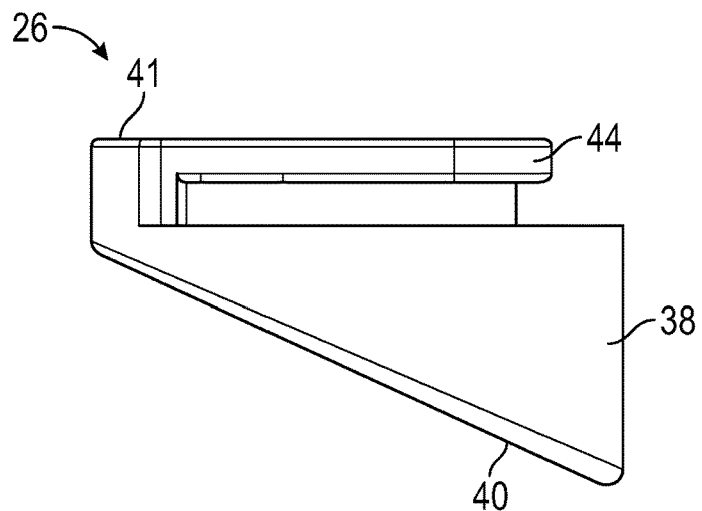
FIG. 8 illustrates a side view of the head assembly of FIG. 5.

The control block 26 includes a block body 38 having a generally elliptical perimeter, as illustrated in FIG. 6. The block body 38 has a generally wedge shaped cross-sectional geometry including a control surface 40 opposed to an engagement surface 41, as illustrated in FIGS. 3-4 and 8. The control block 26 can be a monolithic component, or can be formed from multiple components fixedly attached to each other. The engagement surface 28C of the reaming head 28 is rotatable along the control surface 40 of the control block 26 to remove tissue (see FIGS. 3 and 9).

The block body 38 defines a through bore 42 extending between the control surface 40 and engagement surface 41 along a block axis BA (FIGS. 3-4 and 6-7). The block axis BA can be substantially collinear with the longitudinal axis A in an installed position, as illustrated in FIGS. 3-4. The through bore 42 is dimensioned to at least partially receive the reaming carrier 25 such that the longitudinal axis A intersects the interface 32, as illustrated in FIG. 3.

Figure 7:
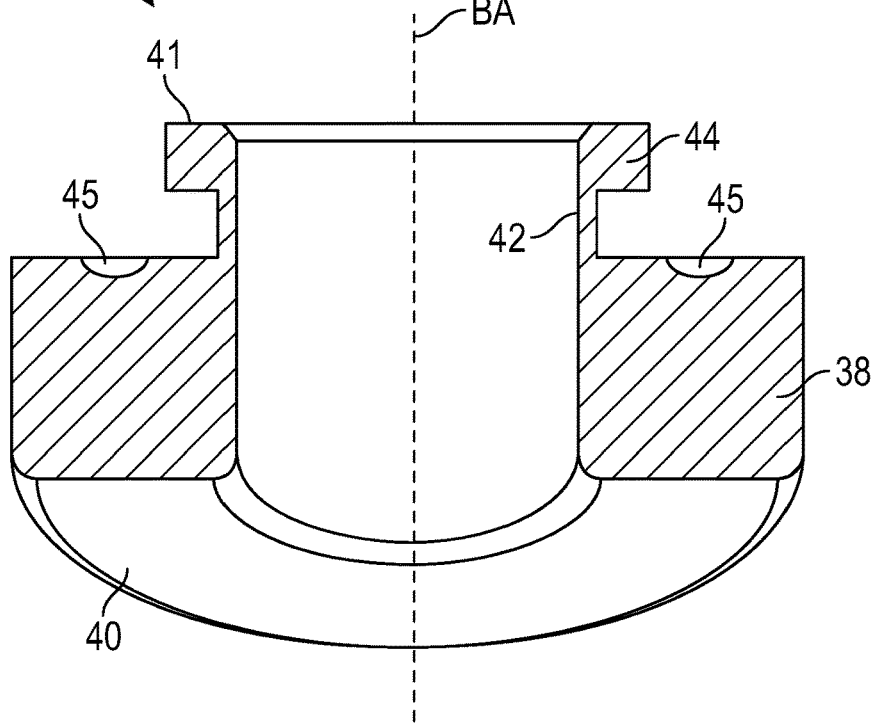
FIG. 7 illustrates a sectional view of the head assembly taken along line 7-7 of FIG. 6.

The control block 26 includes a mounting flange 44 extending outwardly from the block body 38. The mounting flange 44 extends along the block axis BA, as illustrated in FIG. 7, and defines the engagement surface 41. The mounting flange 44 and retention slot 34 have a complementary geometry.

The retention slot 34 is dimensioned to slidably receive or otherwise mate with the mounting flange 44 along the interface 32 to limit axial movement of the control block 26 relative to the longitudinal axis A. The mounting flange 44 is dimensioned such that the block body 38 translates through a projection of the longitudinal axis A in response to moving the mounting flange 44 in a direction D1 (FIG. 4) along the interface 32. The control block 26 is dimensioned to slidably engage the distal end portion 22C of the housing 22 along the interface 32 such that the control surface 40 faces away from the distal end portion 22C. Of course, an opposite configuration is also contemplated in which the housing 22 is at least partially received in the control block 26. Other techniques can be utilized to couple the control block 26 and the housing 22, such as a twist-lock or hinge connection.

Figure 9:
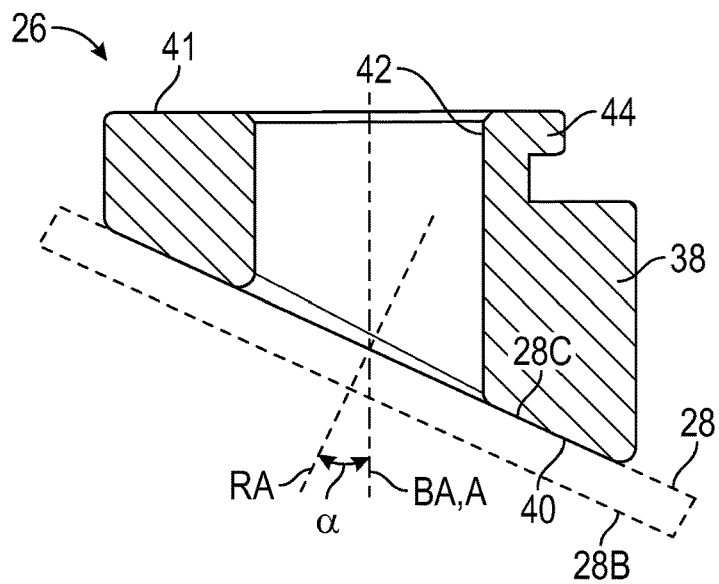
FIG. 9 illustrates a sectional view of the head assembly taken along line 9-9 of FIG. 6.
Figure 10:
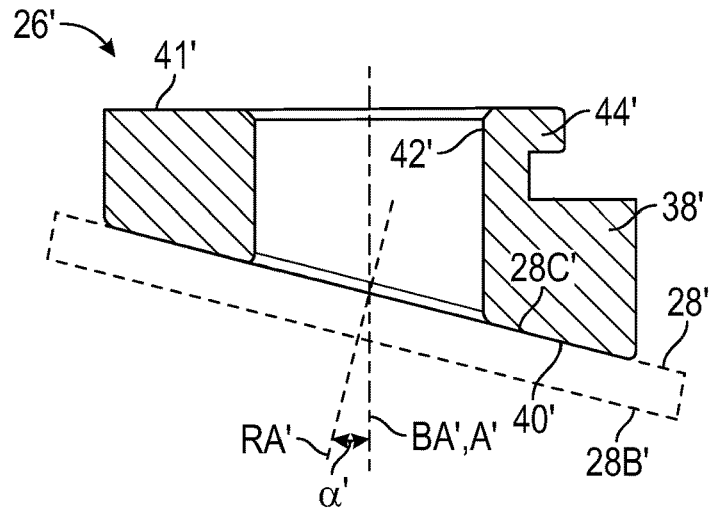
FIG. 10 illustrates a sectional view of a head assembly according to another embodiment.

Referring to FIG. 9, the control surface 40 of the control block 26 is oriented to define a reaming angle α between the longitudinal axis A (or block axis BA) and the reaming axis RA of the reaming head 28 in an installed position (shown in dashed lines for illustrative purposes). The control surface 40 is sloped or non-orthogonal relative to the block axis BA (and the longitudinal axis A in the installed position) such that the reaming angle α has a non-zero value (see also FIG. 8).

The reaming assembly 20 can include a set of control blocks 26 having different reaming angles α. In embodiments, the reaming assembly 20 includes at least one control block 26 defining a reaming angle α that is substantially perpendicular to the block axis BA. In the illustrated embodiment of FIG. 9, a first control block 26 defines a first reaming angle α. In the illustrated embodiment of FIG. 10, a second control block 26' defines a second reaming angle α'. The control blocks 26, 26' can be dimensioned such that the reaming angle α of the control block 26 differs from the reaming angle α' of the control block 26'. For example, the first reaming angle α is greater than the second reaming angle α' of control block 26'. Each reaming angle α, α' is a fixed angle that sets a different orientation of the reaming axis RA, RA' of the reaming head 28, 28' relative to the block axis BA, BA' and/or longitudinal axis A, A'. It should be appreciated that the reaming assembly 20 can include more than two control blocks 26 each having a different reaming angle α, such as a set of control blocks 26 define distinct reaming angles α between 5-45 degrees in 5 or 10 degree increments. One or more reaming kits can be provided with a reaming assembly 20 and various control blocks 26 that provide different reaming angles α.

Figure 11:
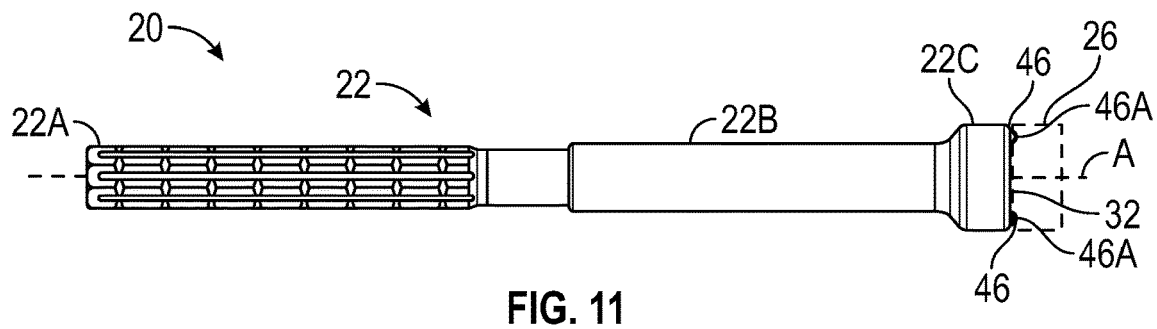
FIG. 11 illustrates a plan view of the housing of the reaming assembly of FIG. 1 including one or more locking members.

Referring to FIG. 11, the reaming assembly 20 can include at least one locking member 46 operable to selectively couple the housing 22 and control block 26. In the illustrated embodiment of FIG. 11, the reaming assembly 20 includes two locking members 46 along the distal end portion 22C of the housing 22 that engage the control block 26 (shown in dashed lines for illustrative purposes). It should be understood that fewer or more than two locking members 46 can be utilized in accordance with the teachings disclosed herein. Of course, an opposite configuration is also contemplated in which the control block 26 includes one or more locking members 46 that engage the housing 22.

Referring to FIGS. 12-13, with continuing reference to FIG. 11, each locking member 46 can be a ball spring assembly that establishes a snap connection. The locking member 46 includes an engagement pin 46A having a generally hemispherical shaped head, a spring member 46B (FIG. 13), and a retention pin 46C. The spring member 46B can be a coil spring as illustrated in FIG. 13, or another spring such as a torsion spring, for example. The engagement pin 46A and spring member 46B are at least partially received in a bore 37 (FIG. 13) defined in the distal end portion 22C of the housing 22. Each retention pin 46C is at least partially received in a respective aperture 39 defined in a sidewall of the distal end portion 22C of the housing 22 to limit or otherwise oppose movement of the engagement pin 46A relative to the housing 22.

Figure 14A:
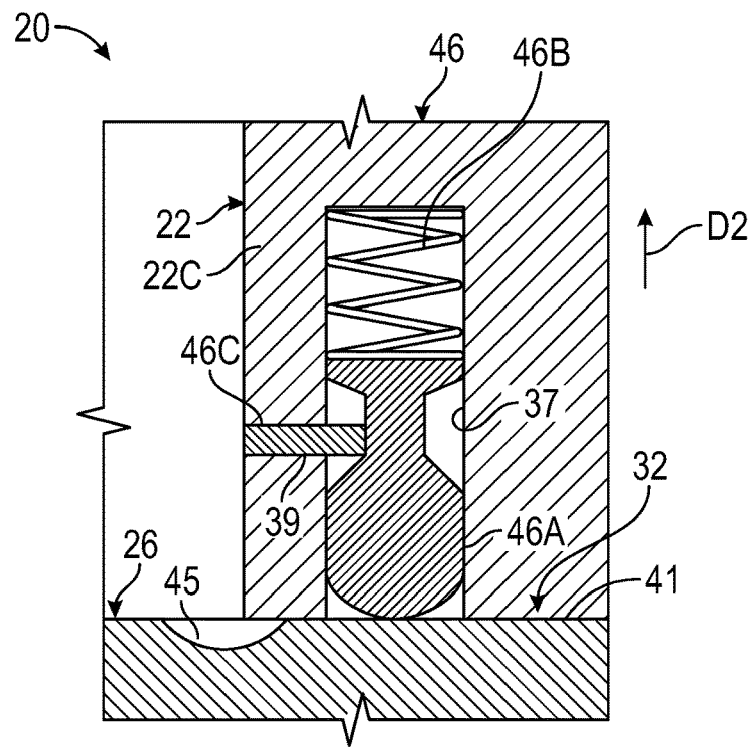
FIG. 14A illustrates a sectional view of one of the locking members of FIG. 11 at a first position.
Figure 14B:
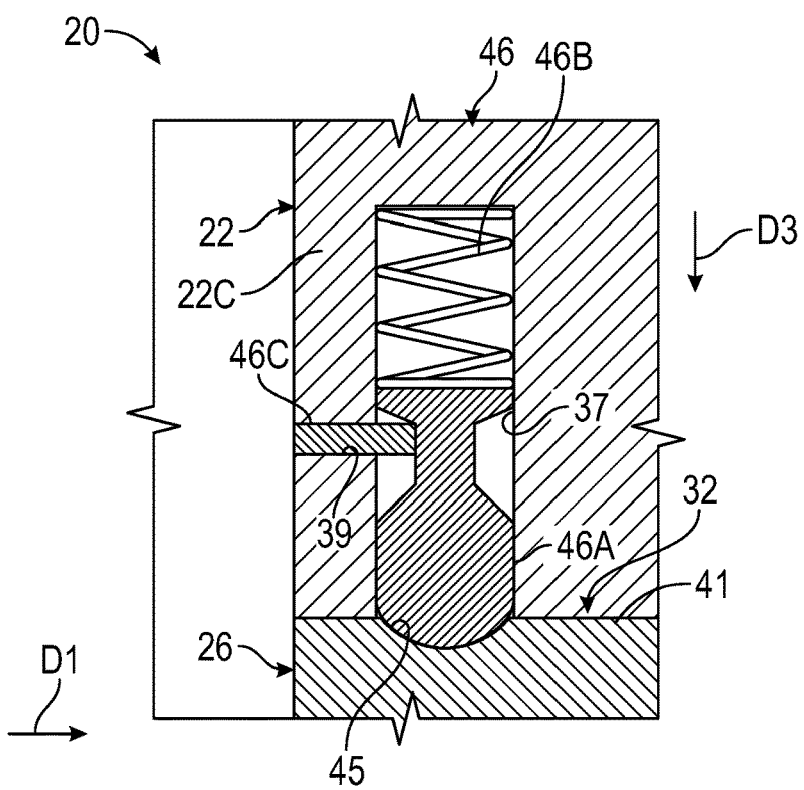
FIG. 14B illustrates a sectional view of the locking member of FIG. 14A at a second position.

Referring to FIGS. 14A-14B, with continuing reference to FIGS. 11-13, the spring member 46B is operable to bias or urge the engagement pin 46A outwardly of the bore 37. Each engagement pin 46A is moveable between a retracted position and an extended position, as illustrated by FIGS. 14A and 14B, respectively.

In the retracted position (FIG. 14A), the engagement pin 46A moves in a direction D2 in response to contact with the engagement surface 41 of the control block 26 along the interface 32, causing the spring member 46B to at least partially compress. The engagement pin 46A is spaced a distance from a respective depression 45 that extends inwardly from the engagement surface 41 of the control block 26 (see also FIGS. 5-7). The depression 45 can be dimensioned to have a complementary geometry with an end portion of the engagement pin 46A. Each depression 45 can be spaced a distance from the mounting flange 44, as illustrated in FIGS. 6-7.

In the extended position (FIG. 14B), the depression 45 is substantially aligned with the end portion of the engagement pin 46A. The spring member 46B causes the engagement pin 46A to move outwardly in a direction D3, which causes the end portion of the engagement pin 46A to be at least partially received in the depression 45. The engagement pin 46A extends across the interface 32 to oppose movement of the control block 26 relative to the housing 22 along the interface 32.

Figure 15:
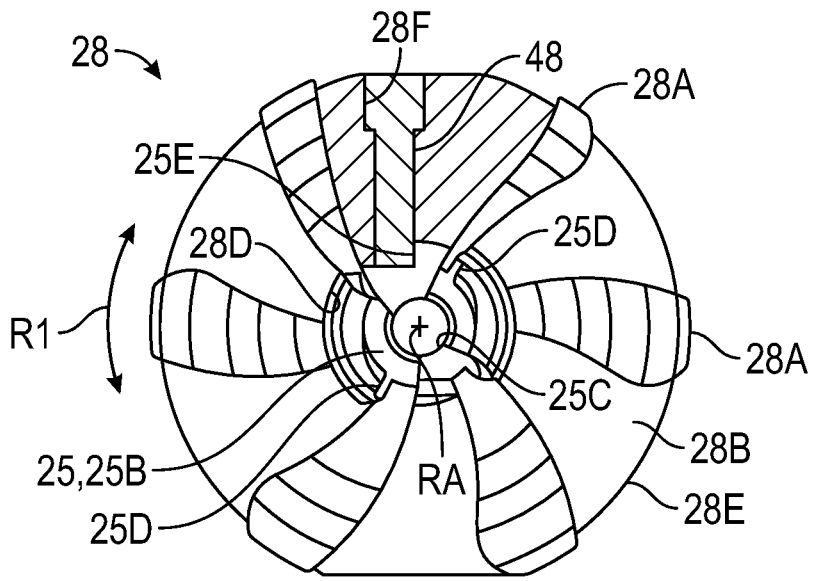
FIG. 15 illustrates an end view of a reaming head of the reaming assembly of FIG. 1.
Figure 16:
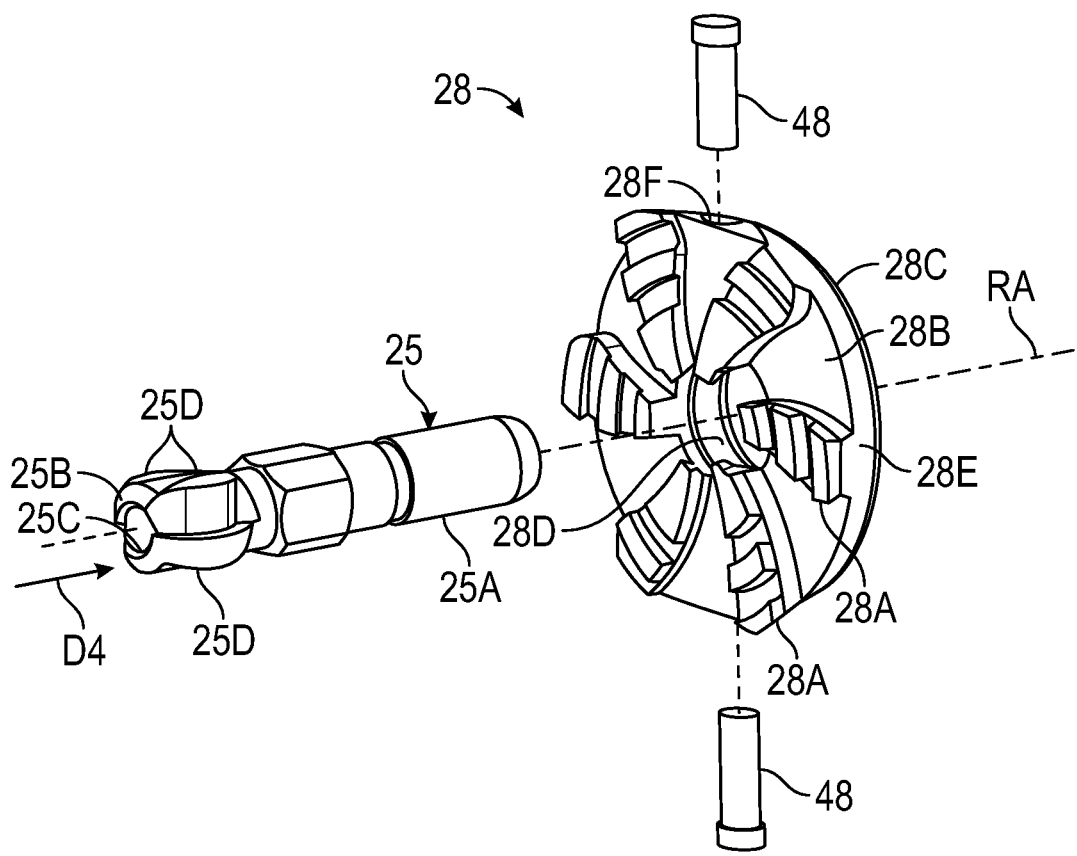
FIG. 16 illustrates an exploded view of the reaming head of FIG. 15.

Referring to FIGS. 15-16, with continuing reference to FIG. 3, the reaming carrier 25 includes an elongated drive portion 25A extending from a head portion 25B. The drive portion 25A is fixedly attached or otherwise secured to the drive shaft 24, as illustrated in FIG. 3. The reaming carrier 25 includes a passageway 25C that extends along the reaming axis RA between opposed ends of the drive and head portions 25A, 25B. The passageway 25C can be dimensioned to receive a guide pin GP (see FIG. 3).

The reaming carrier 25 is partially received in a bore 28D defined in the reaming head 28. The bore 28D extends along the reaming axis RA. The plurality of teeth 28A extend between the bore 28D and an outer periphery 28E of the reaming head 28. An outer periphery of the drive portion 25A can include one or more protrusions or engagement features 25D dimensioned to mesh with or otherwise engage the teeth 28A adjacent to the bore 28D, as illustrated in FIG. 15. The engagement features 25D can serve to improve torque transfer between the reaming carrier 25 and the reaming head 28.

One or more retention pins 48 are received in respective bores 28F defined in the reaming head 28, as illustrated in FIGS. 3 and 15. Each retention pin 48 is dimensioned to abut against a shoulder 25E of the head portion 25B of the reaming carrier 25, as illustrated in FIG. 15, and establishes a hinge joint or pivotable coupling between the reaming head 28 and the reaming carrier 25.

Figure 17:
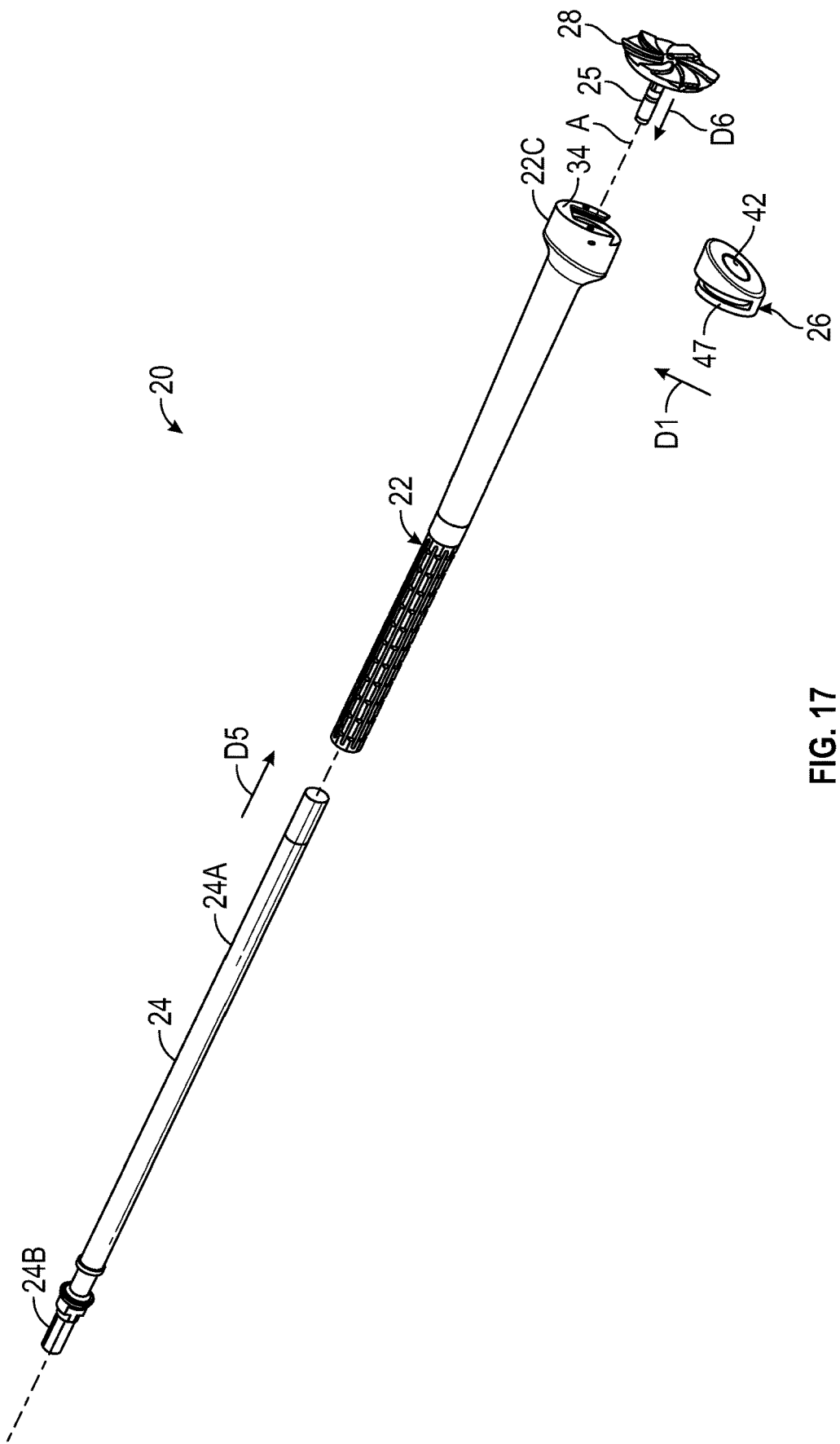
FIG. 17 illustrates a partially exploded view of the reaming assembly of FIG. 1.
Figure 18:
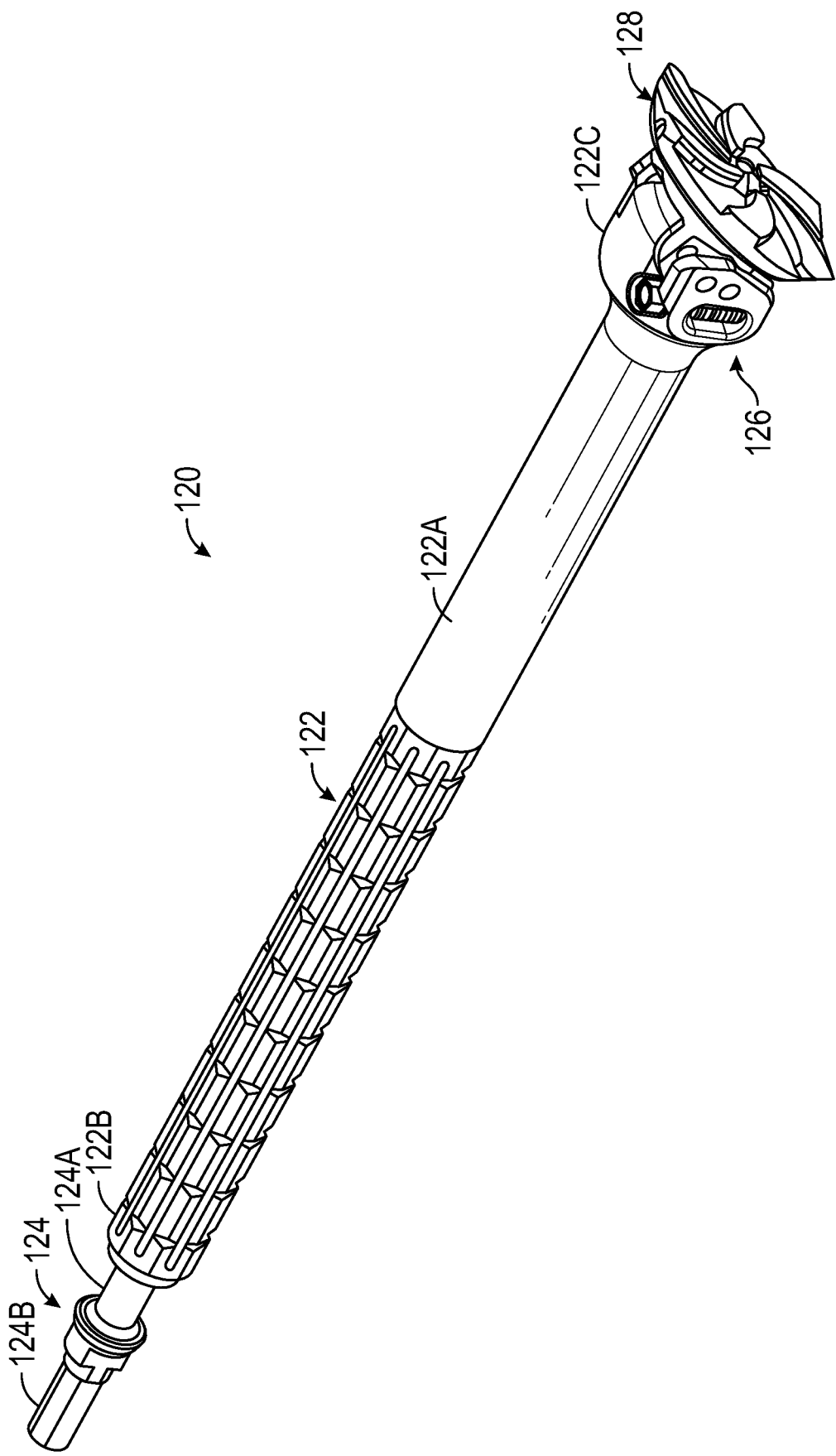
FIG. 18 illustrates a perspective view of an exemplary reaming assembly according to another embodiment.

Referring to FIG. 17, the reaming assembly 20 can be assembled as follows. A control block 26 can be selected from a set of control blocks 26 to orient the reaming head 28 relative to a respective reaming angle α (see, e.g., 26, 26' of FIGS. 9-10). In embodiments, the set of control blocks 26 include ten control blocks 26 having fixed reaming angles α in 2.5 degree increments between 0 degrees and 25 degrees. It should be appreciated that the reaming assembly 20 can include fewer or more than ten control blocks 26 having a different range of reaming angles α values and increments. The control block 26 is moved in direction D1 toward the longitudinal axis A such that the mounting flange 44 is inserted into the retention slot 34 of the housing 22, the control block 26 is moved through a projection of the longitudinal axis A, and the mounting flange 44 is brought into abutment with a sidewall of the retention slot 34, as illustrated in FIG. 4. In an assembled position, the reaming head 28 extends distally of the control block 26 relative to the longitudinal axis A, with the control block 26 trapped between the distal end portion 22C of the housing 22 and the engagement surface 28C of the reaming head 28, as illustrated in FIGS. 2-3.

The shaft portion 24A of the drive shaft 24 is moved in direction D5 along the longitudinal axis A and is inserted into the passageway 30, as illustrated in FIG. 2. The reaming carrier 25 together with the reaming head 28 is moved in a direction D6 along the longitudinal axis A such that the reaming carrier 25 is inserted into and through the bore 42 of the control block 26, into the passageway 30, and at least partially into a region 24D of the inner bore 24C of the shaft portion 24A, as illustrated in FIG. 3. The shaft portion 24A of the drive shaft 24 and reaming carrier 25 are fixedly attached or otherwise operably coupled to each other to limit relative rotation. Thereafter, tooling T1 (FIG. 2) is coupled to the interface portion 24B of the drive shaft 24 to selectively rotate the drive shaft 24 about the longitudinal axis A and the and reaming head 28 about the reaming axis RA (FIG. 3).

FIGS. 18-27 illustrate an exemplary reaming assembly 120 according to another embodiment. Referring to FIGS. 18-21, the reaming assembly 120 includes a housing 122, a rotatable drive shaft 124 at least partially received in a passageway 130 (FIG. 21) of the housing 122, a head assembly 126 coupled to the housing 122, and a reaming head 128 pivotably attached to reaming carrier 125. The drive shaft 124 can be a cannulated drive shaft including an inner bore 124C (FIGS. 21-22) dimensioned to at least partially receive a guide pin. The reaming carrier 125 is operably coupled to the reaming head 128.

The head assembly 126 is coupled to a distal end portion 122C of the housing 122. The head assembly 126 is operable to set an orientation of the reaming head 128 relative to the longitudinal axis A.

Figure 19:
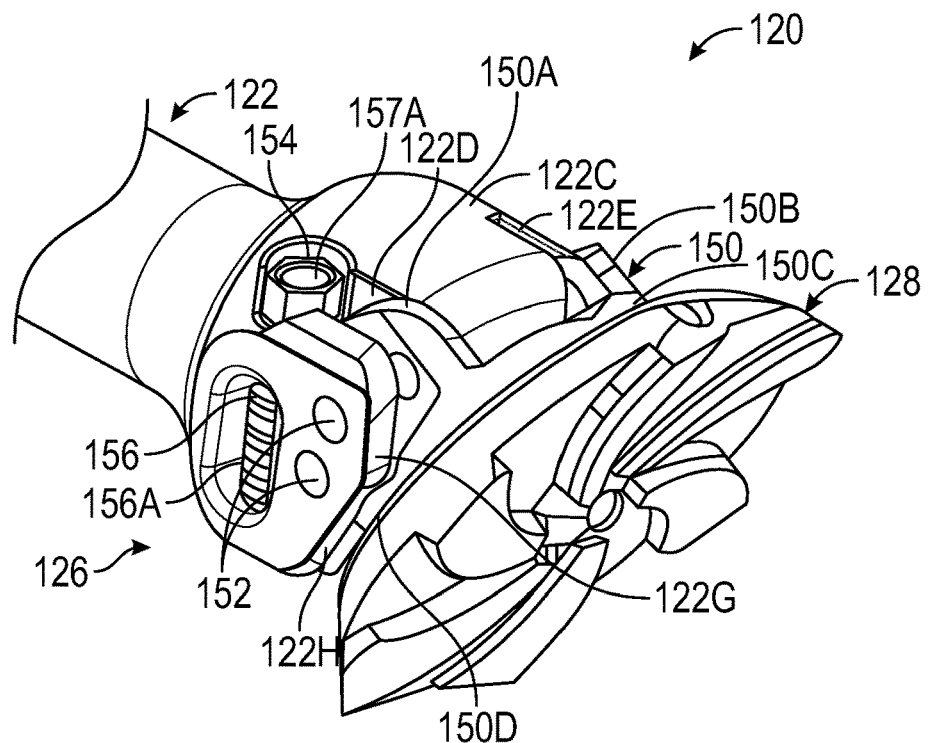
FIGS. 19-20 illustrate perspective views of selected portions of the reaming assembly of FIG. 18.
Figure 20:
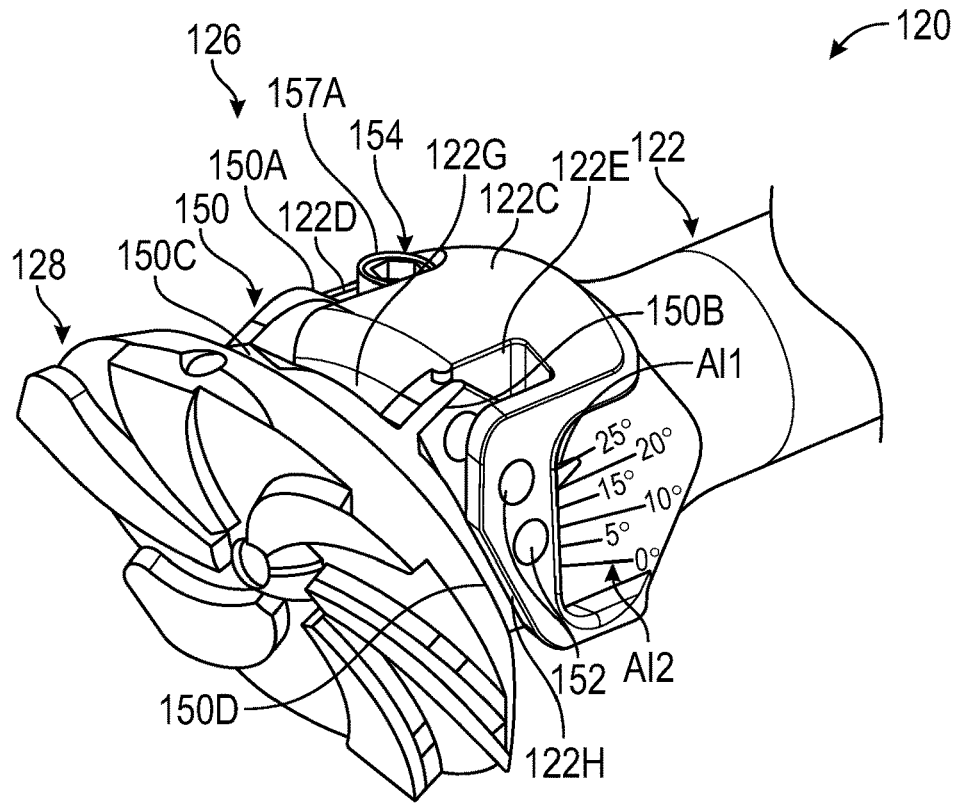

Referring to FIGS. 19-20, the head assembly 126 includes a head plate 150 having a control flange 150A and mounting flange 150B each extending outwardly from a plate body 150C. The distal end portion 122C of the housing 122 defines a pair of recesses 122D, 122E dimensioned to at least partially receive the flanges 150A, 150B. The plate body 150C defines a control surface 150D dimensioned to abut against an engagement surface 128C of the reaming head 128 to set an orientation of the reaming head 128 (see FIG. 21).

Figure 21:
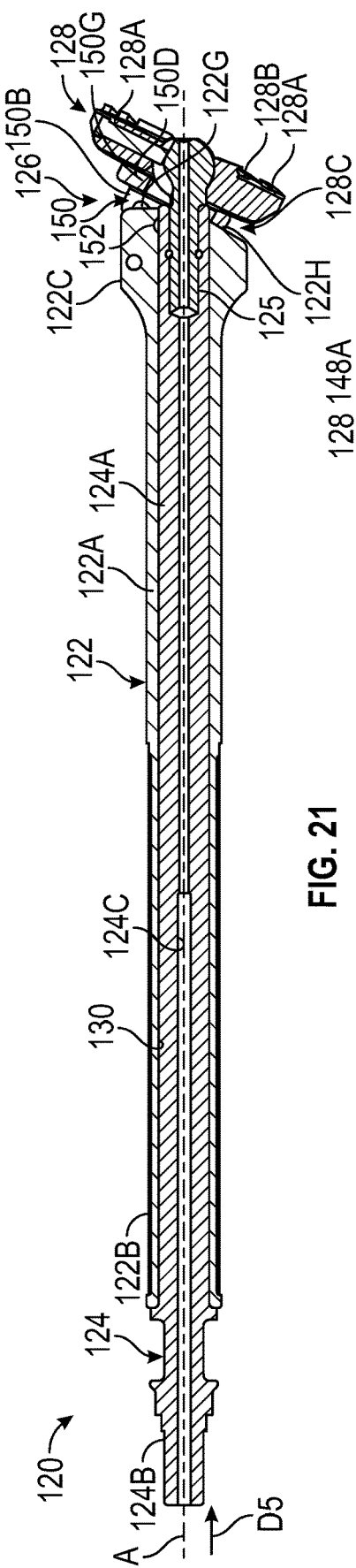
FIG. 21 illustrates a sectional view of the reaming assembly of FIG. 18.
Figure 22:
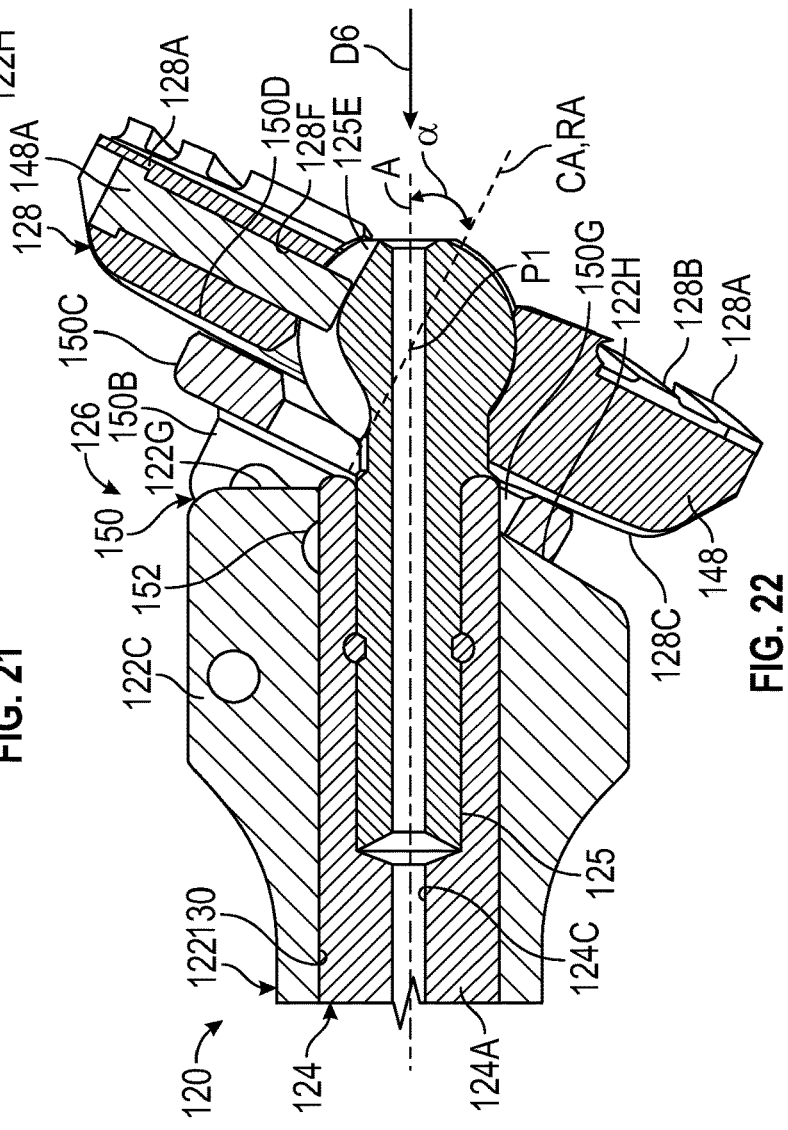
FIG. 22 illustrates selected portions of the reaming assembly of FIG. 21.

Referring to FIGS. 21-22, with continuing reference to FIGS. 19-20, reaming carrier 125 is dimensioned to extend through an opening 150G defined in the control surface 150D. The reaming carrier 125 is pivotally attached to the reaming head 128 along the longitudinal axis A to operably couple the drive shaft 124 and the reaming head 128. The head plate 150 defines a control axis CA (FIG. 22) extending through the opening 150G. The reaming head 128 is rotatable about a reaming axis RA (FIG. 22) in response to rotation of the drive shaft 124 and reaming carrier 125 about the longitudinal axis A. The control axis CA can be collinear or otherwise parallel with the reaming axis RA, as illustrated in FIG. 22. The reaming axis RA intersects the longitudinal axis A at a position P1 (FIG. 22) in the bore 128D distally of the head plate 150. The reaming head 128 is rotatable along the control surface 150D to remove tissue such as bone. The control surface 150D faces away from the housing 122 when the reaming head 128 is in an installed position.

Figure 23:
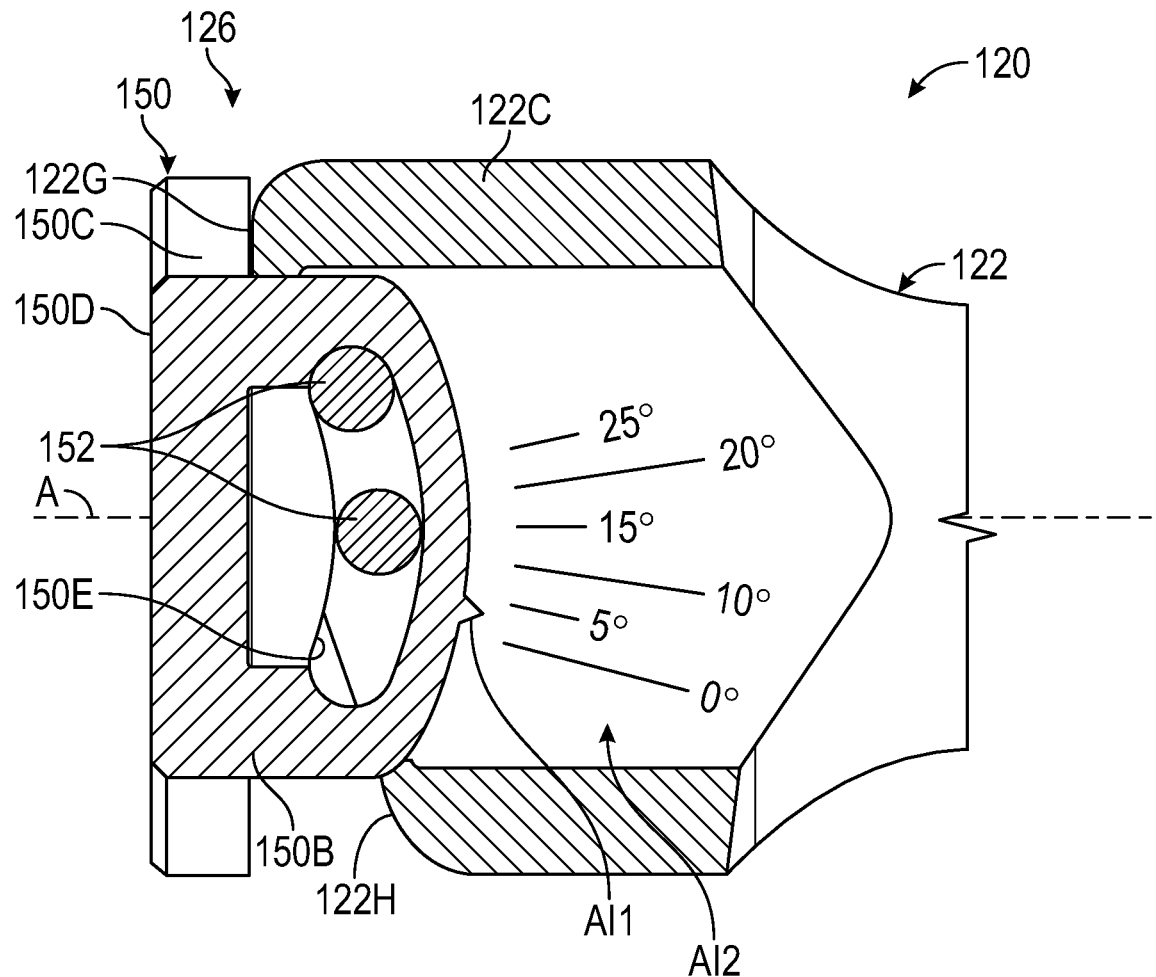
FIG. 23 illustrates a sectional view of a head assembly of the reaming assembly of FIG. 18.
Figure 24A:
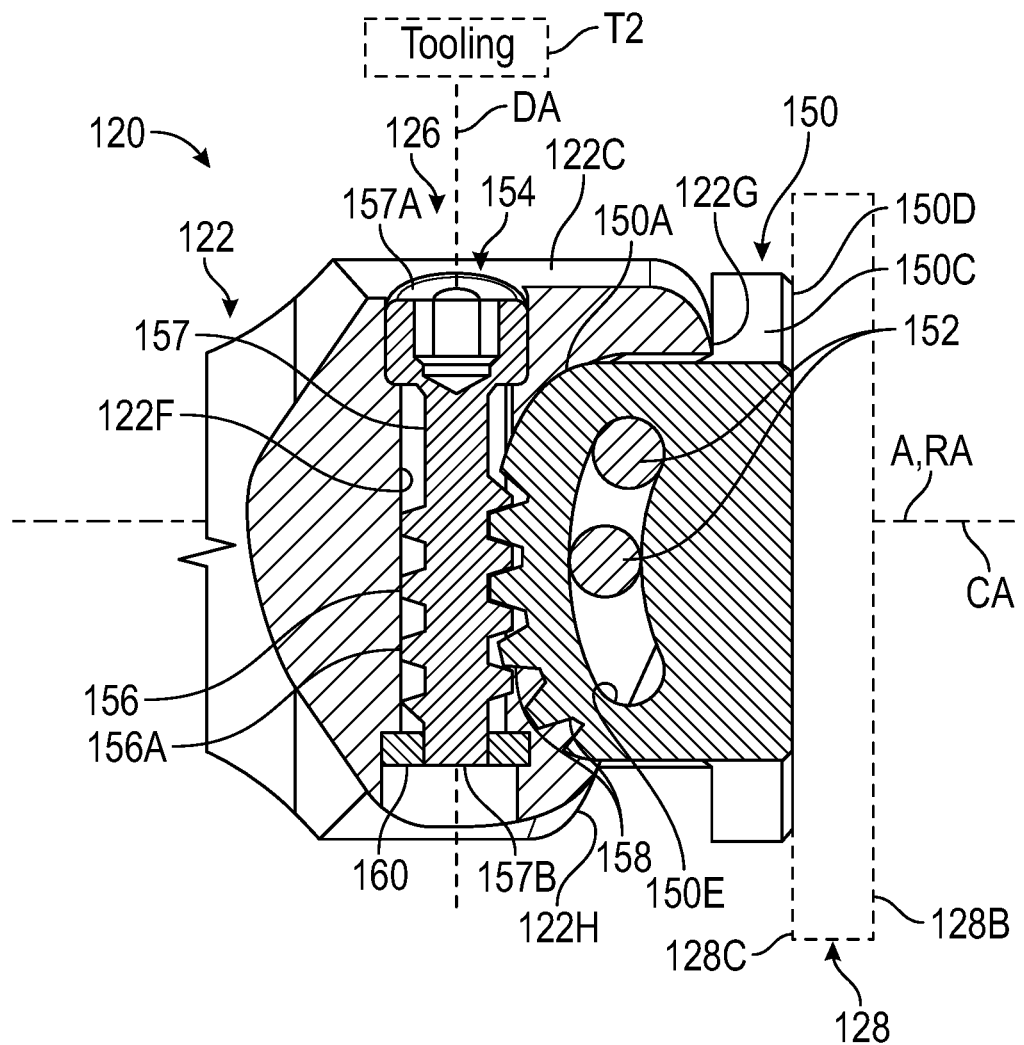
FIGS. 24A-24C illustrates sectional views of the head assembly of FIG. 18 including a head plate and reaming head at different orientations.

Referring to FIGS. 23 and 24A, with continuing reference to FIGS. 19-22, the flanges 150A, 150B can be pivotably attached to the distal end portion 122C of the housing 122 utilizing one or more fasteners or support pins 152. The flanges 150A, 150B define respective grooves 150E, 150F each dimensioned to receive one or more of the support pins 152. Each support pin 152 is fixedly attached or otherwise secured to the distal end portion 122C of the housing 122. Each groove 150E, 150F can have a generally arcuate shape and is dimensioned to receive two support pins 152 at different axially and radial positions relative to the longitudinal axis A. Each groove 150E, 150F can be dimensioned to receive fewer or more than two support pins 152.

Figure 25:
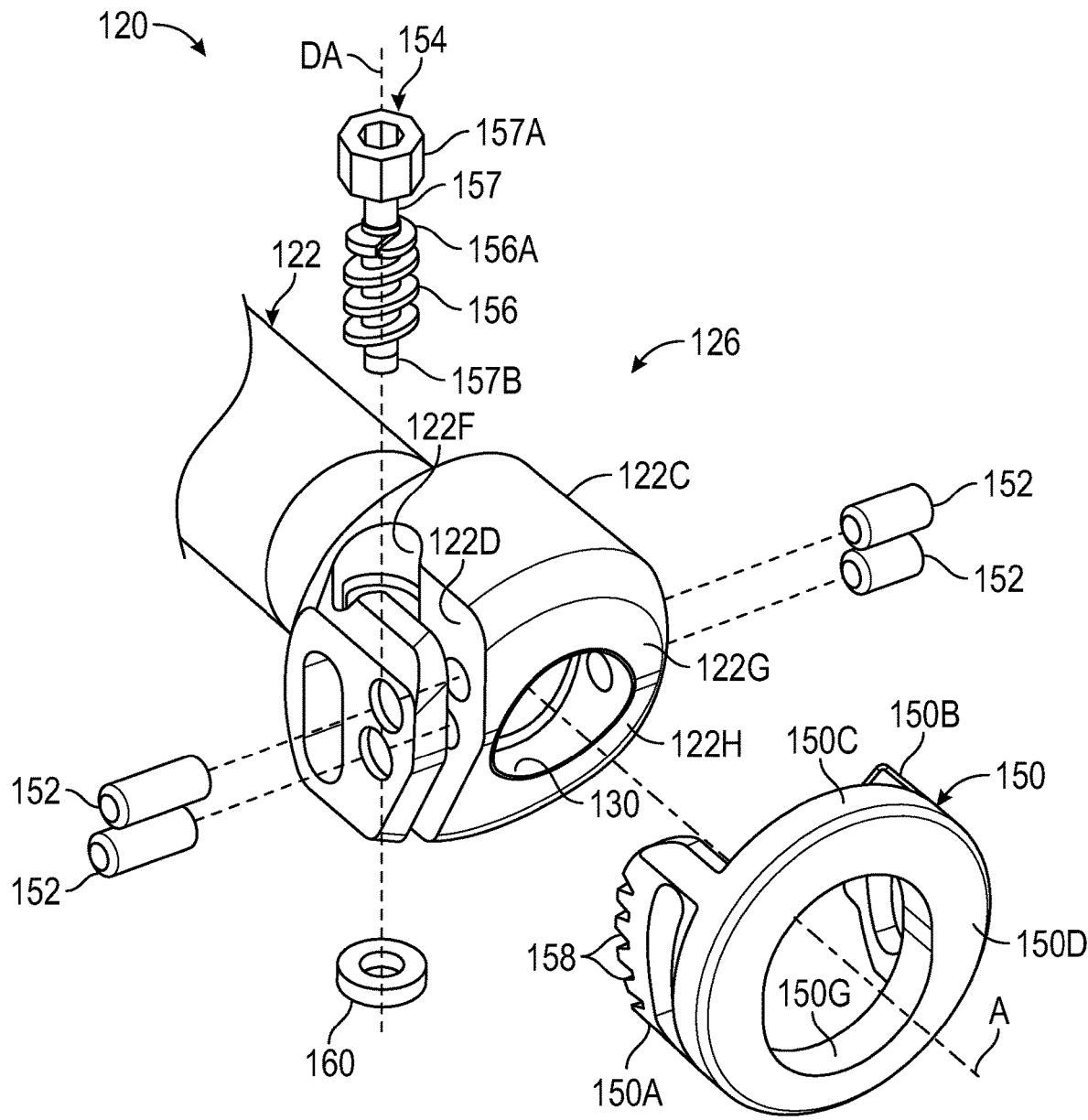
FIG. 25 illustrates an exploded view of the head assembly of FIGS. 24A-24C.

Referring to FIGS. 24A and 25, with continuing reference to FIG. 19, the head assembly 126 includes a drive member 154 operable to selectively adjust an orientation of the control surface 150D of the head plate 150 relative to the longitudinal axis A. The drive member 154 includes a worm drive 156 and a worm shaft 157 extending along a drive axis DA. The worm drive 156 and worm shaft 157 are at least partially received in a bore 122F defined in the housing 122 such that the drive axis DA is substantially perpendicular or otherwise transverse to the longitudinal axis A.

The drive member 154 is dimensioned to engage the control flange 150A adjacent the bore 122F. The worm drive 156 has threading 156A that spirals or otherwise extends about an outer diameter of the worm shaft 157. The threading 156A of the worm drive 156 serves as a worm screw that meshes with a worm wheel or plurality of engagement teeth 158 along the control flange 150A.

The worm shaft 157 includes a head portion 157A dimensioned to engage tooling T2 (shown in dashed lines for illustrative purposes) to rotate the worm drive 156 and worm shaft 157 about the drive axis DA to cause the head plate 150 to tilt or pivot relative the distal end portion 122C of the housing 122. In embodiments, the head portion 157A and tooling T2 establish a socket connection to transfer torque to the worm drive 156. An end portion 157B of the worm shaft 157 opposed to the head portion 157A can be threadably secured to a nut 160 to secure the drive member 154 to the housing 122.

Figure 24B:
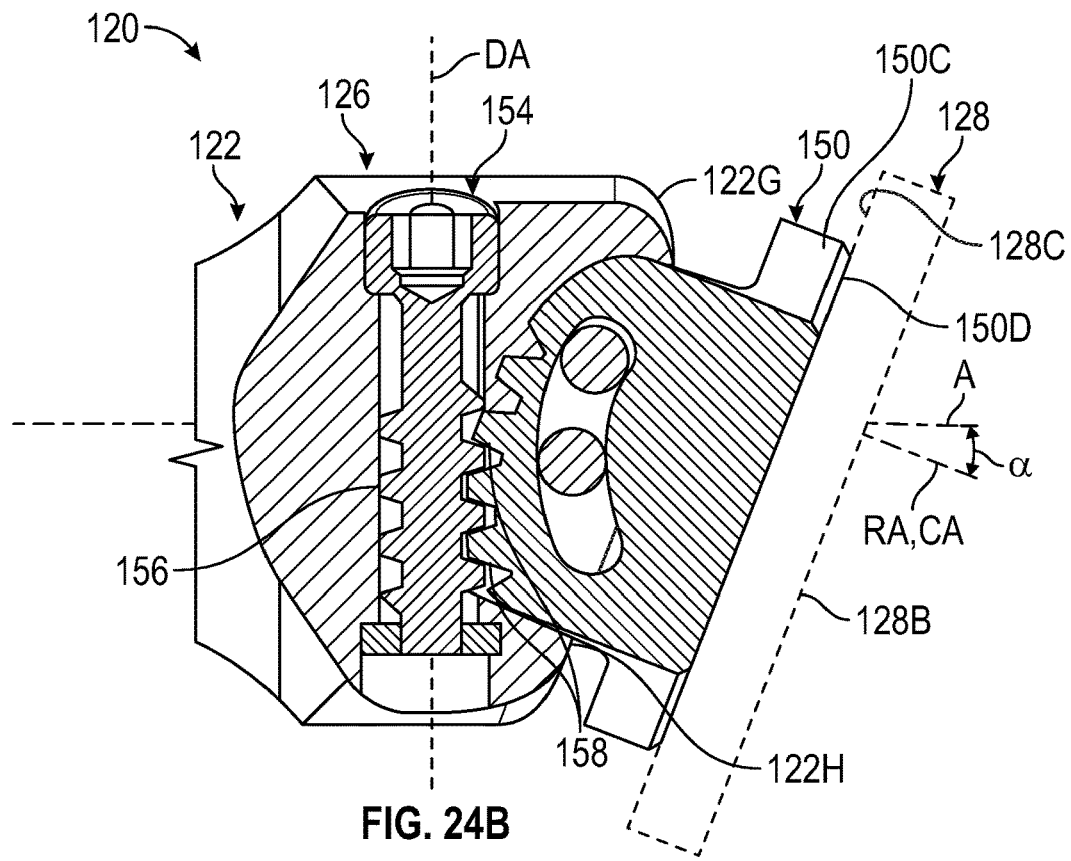
Figure 24C:
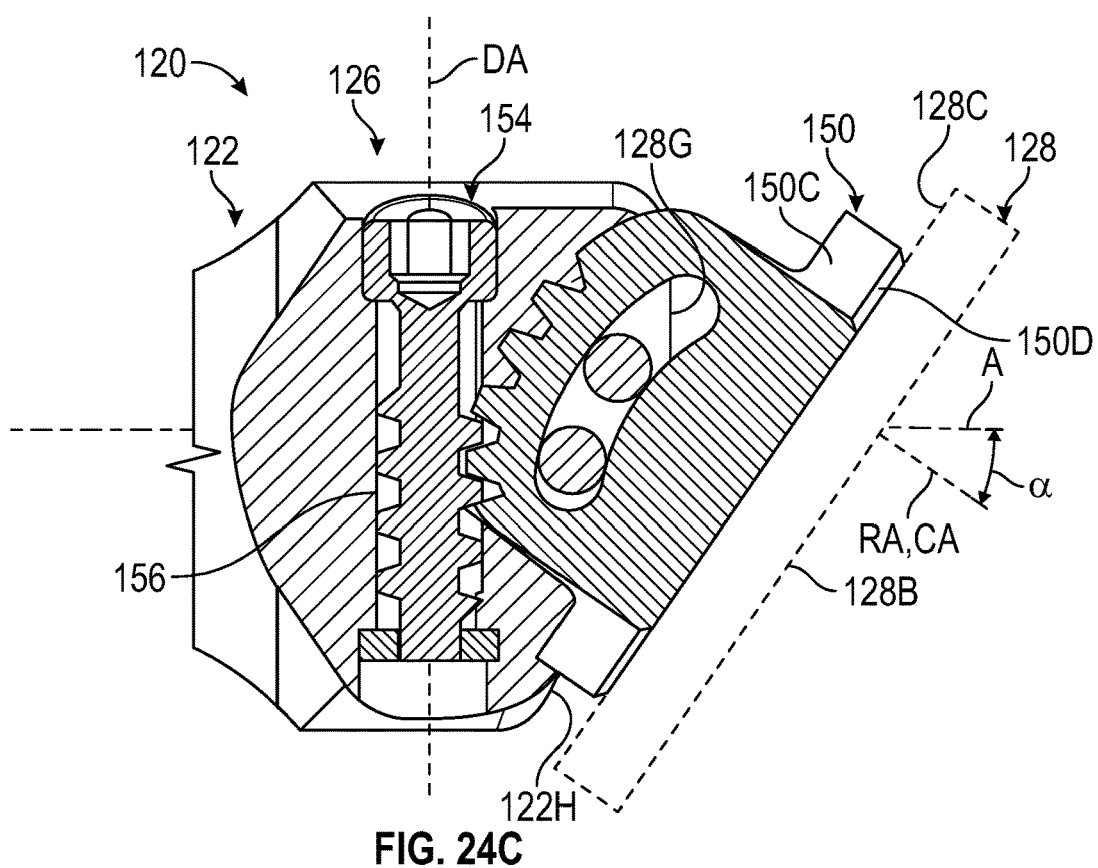

The head plate 150 is pivotable between a minimum angle and a maximum angle relative to the longitudinal axis A to set or select a reaming angle α (FIGS. 24B-24C) of the reaming head 128 (shown in dashed lines in FIGS. 24A-24C for illustrative purposes) in response to translation of the engagement teeth 158 along the worm drive 156. The control flange 150A adjusts an orientation of the control surface 150D relative to the longitudinal axis A and the reaming angle α in response to rotation of the worm drive 156 about the drive axis DA. The reaming angle α is defined between the longitudinal axis A and the reaming axis RA (or the control axis CA when the reaming head 128 is in an uninstalled position). FIG. 24A illustrates the reaming head 128 pivoted at a first position corresponding to the minimum angle. FIG. 24C illustrates the reaming head 128 pivoted at a second position corresponding to the maximum angle. FIG. 24B illustrates the reaming head 128 pivoted at a third position corresponding to a reaming angle α having a value between the minimum and maximum angles. In the embodiments of FIGS. 24B and 24C, the control surface 150D is non-orthogonal relative to the longitudinal axis A.

The distal end portion 122C of housing 122 can include first and second engagement surfaces 122G, 122H that face towards the plate body 150C of the head plate 150 (see also FIGS. 19-22). The first engagement surface 122G can be oriented substantially perpendicular to the longitudinal axis A, and the second engagement surface 122H can slope away from the first engagement surface 122G such that the second engagement surface 122H is transverse to the longitudinal axis A, as illustrated in FIGS. 22 and 25.

The first and/or second engagement surfaces 122G, 122H can be dimensioned to limit pivoting or rotation of the head plate 150 relative to the longitudinal axis A. Abutment between the head plate 150 and the first engagement surface 122G can define a minimum reaming angle α (e.g., approximately 0 degrees), as illustrated by the reaming head 128 in FIG. 24A. Abutment between the head plate 150 and the second engagement surface 122H can define a maximum reaming angle α (e.g., approximately 25 degrees), as illustrated by the reaming head 128 in FIG. 24C. For the purposes of this disclosure, the term "approximately" means ±3% of the stated value unless otherwise disclosed. The drive shaft 124 and reaming carrier 125 can be substantially rigid and can be substantially straight when the head plate 150 is positioned at the maximum reaming angle α, as illustrated in FIGS. 21 and 22.

The reaming assembly 120 can include one or more indicators to identify the present reaming angle α of the reaming head 128. In the illustrative embodiment of FIGS. 20 and 23, the head plate 150 includes an angle indicator AI1 that extends outwardly from the mounting flange 150B. The distal end portion 122C of the housing 122 includes an angular scale AI2 corresponding to a range of reaming angles α that may be selected by the surgeon to set an orientation of the reaming head 128. The angular scale AI2 can range between approximately 0 degrees and 25 degrees in 5 degree increments, for example. It should be appreciated that a minimum angle of the angular scale AI2 can be greater than 0 degrees, such as approximately 5 or 10 degrees, and a maximum angle of the angular scale AI2 can be lesser or greater than 25 degrees, such as approximately 35 or 45 degrees. The head plate 150 can be pivoted such that the angle indicator AI1 is aligned with a position along the angular scale AI2 to select or set the reaming angle α.

Figure 26:
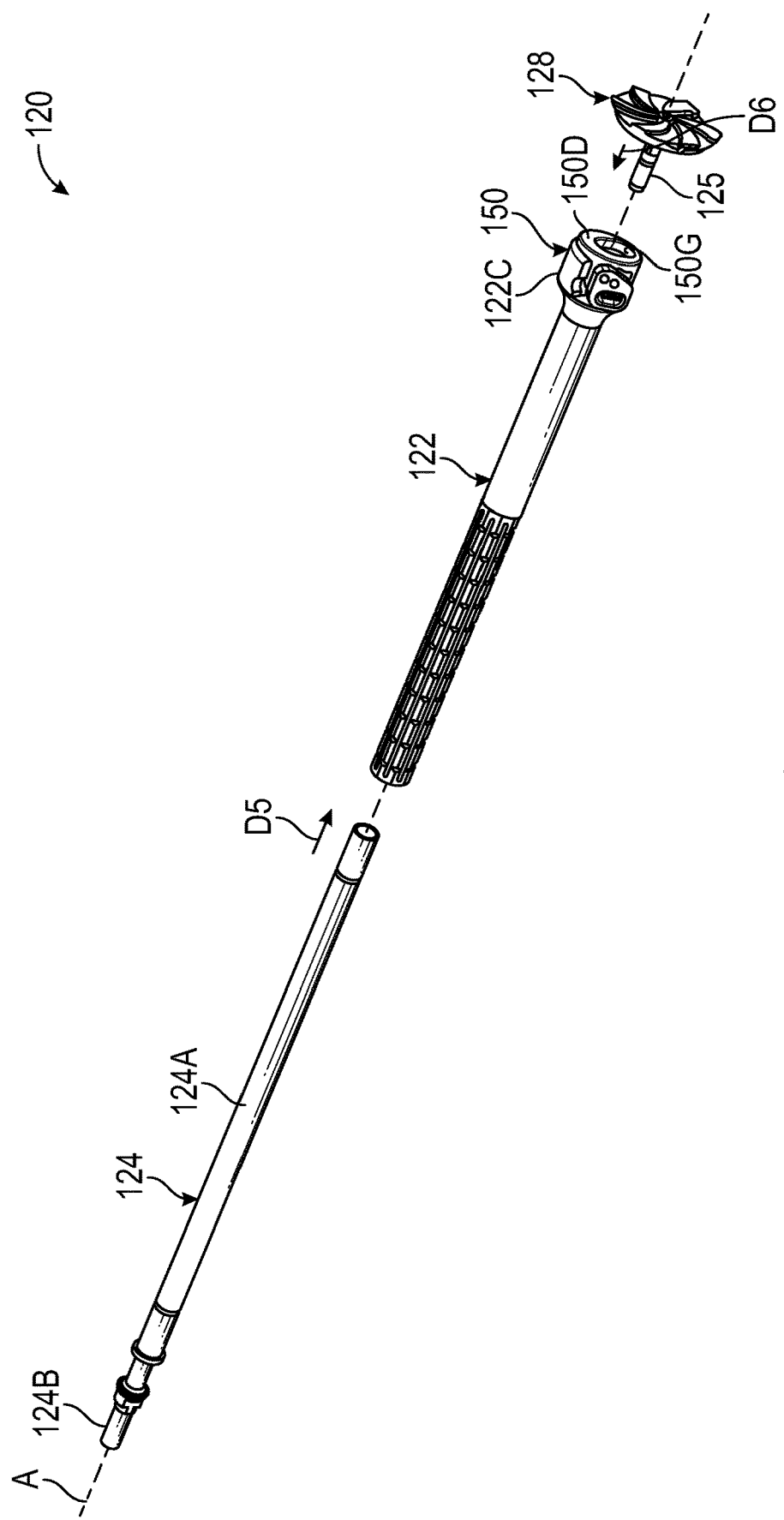
FIGS. 26-27 illustrate partially exploded views of the reaming assembly of FIG. 18.
Figure 27:
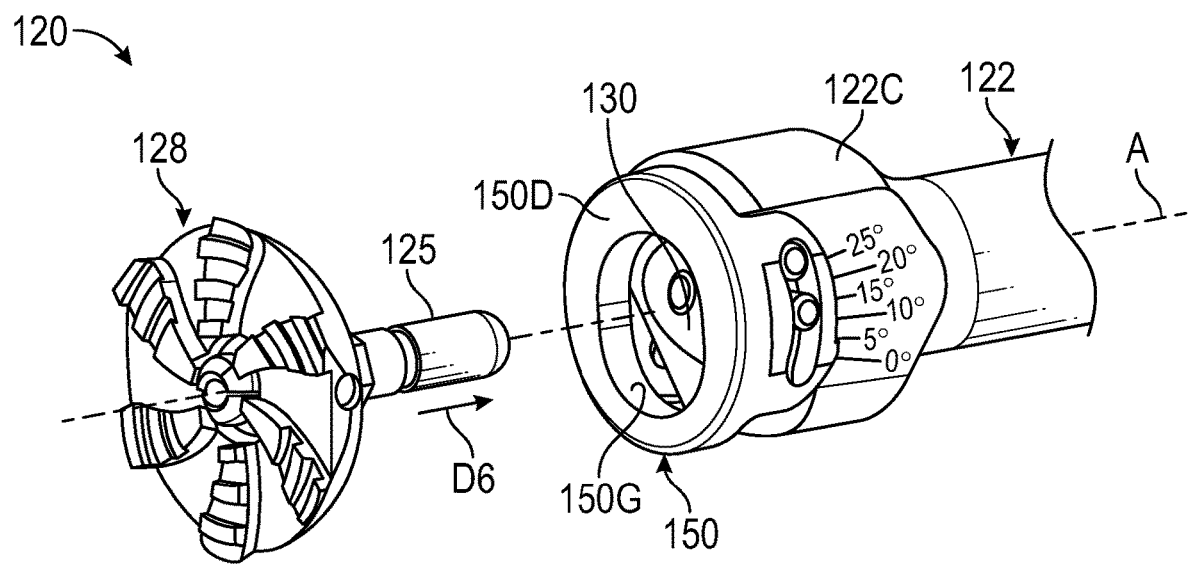

Referring to FIGS. 26-27, with reference to FIG. 21, the reaming assembly 120 can be assembled as follows. The shaft portion 124A of the drive shaft 124 is moved in a direction D5 (FIGS. 21 and 26) along the longitudinal axis A and is inserted into the passageway 130 of the housing 122. The reaming carrier 125 along with the reaming head 128 is moved in a direction D6 (FIGS. 22 and 27) along the longitudinal axis A such that the reaming carrier 125 extends through the opening 150G of the head plate 150 and into the passageway 130 of the housing 122. The reaming head 128 is brought into abutment with the control surface 150D, as illustrated in FIG. 22. The reaming carrier 125 is fixedly attached to the shaft portion 124A of the drive shaft 124 within the passageway 130, as illustrated in FIGS. 21-22.

Figure 28:
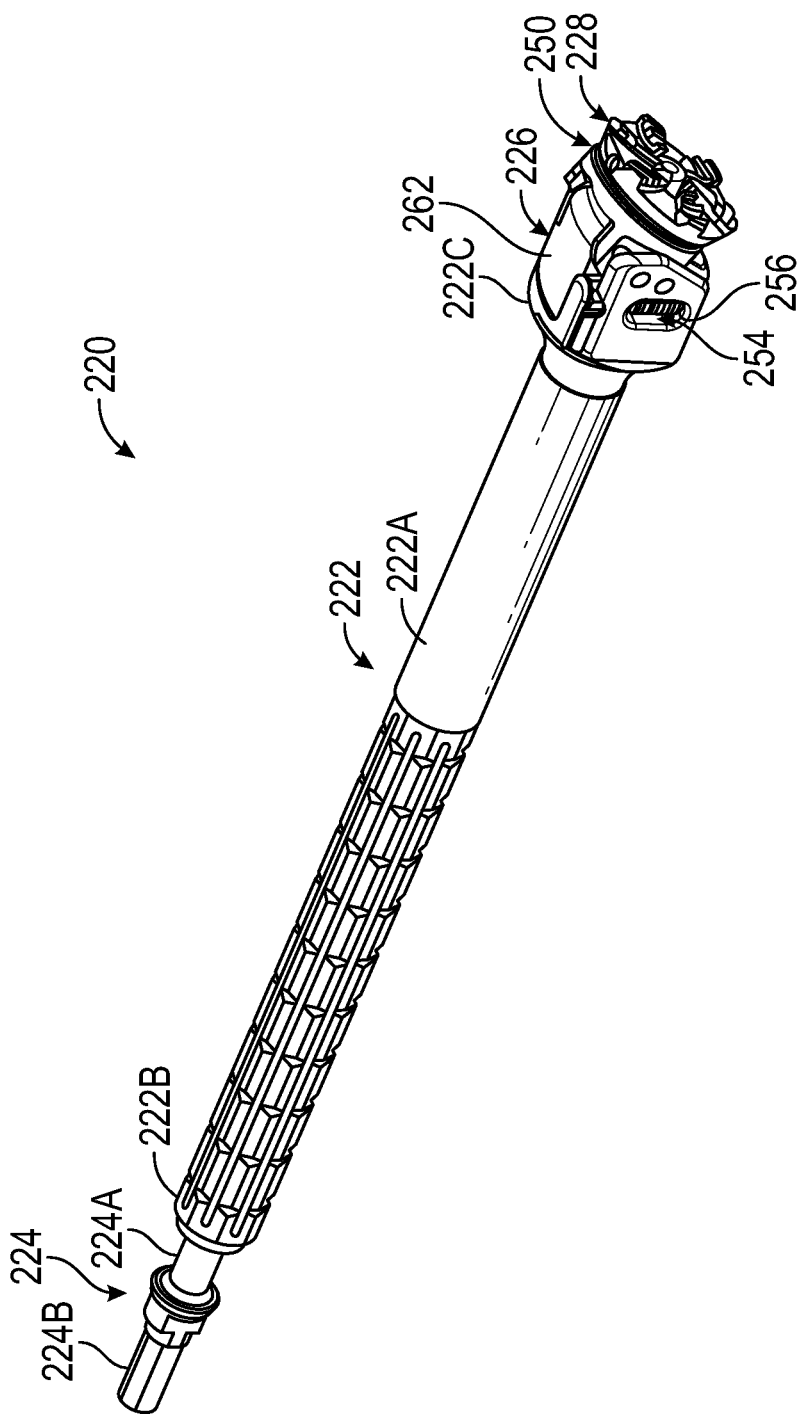
FIG. 28 illustrates a perspective view of an exemplary reaming assembly according to yet another embodiment.

FIGS. 28-31 illustrate an exemplary reaming assembly 220 according to another embodiment. The reaming assembly 220 includes a removable head assembly similar to the reaming assembly 20 and includes a variable angle feature similar to the reaming assembly 120. Referring to FIG. 28, the reaming assembly 220 includes a housing 222, a rotatable drive shaft 224, a head assembly 226 releasably secured to a distal end portion 222C of the housing 222, and a reaming head 228.

Figure 29:
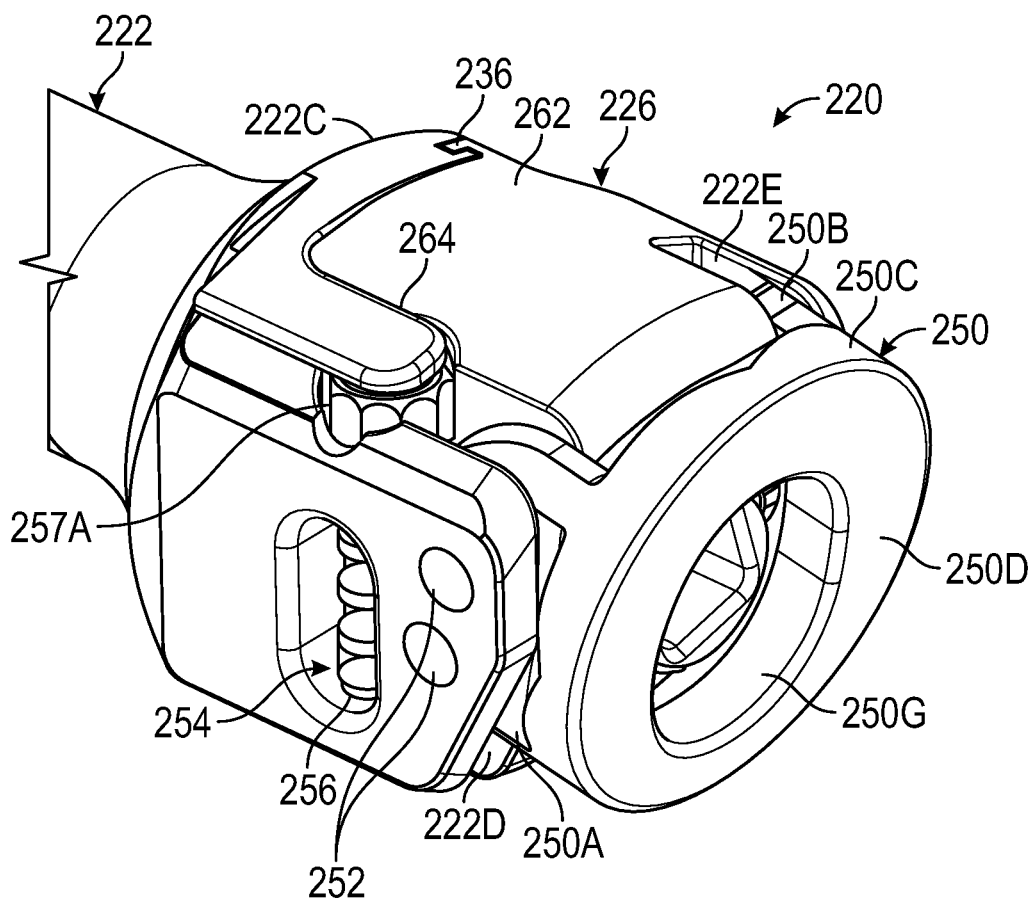
FIG. 29 illustrates a head assembly of the reaming assembly of FIG. 28 in an installed position.
Figure 30:
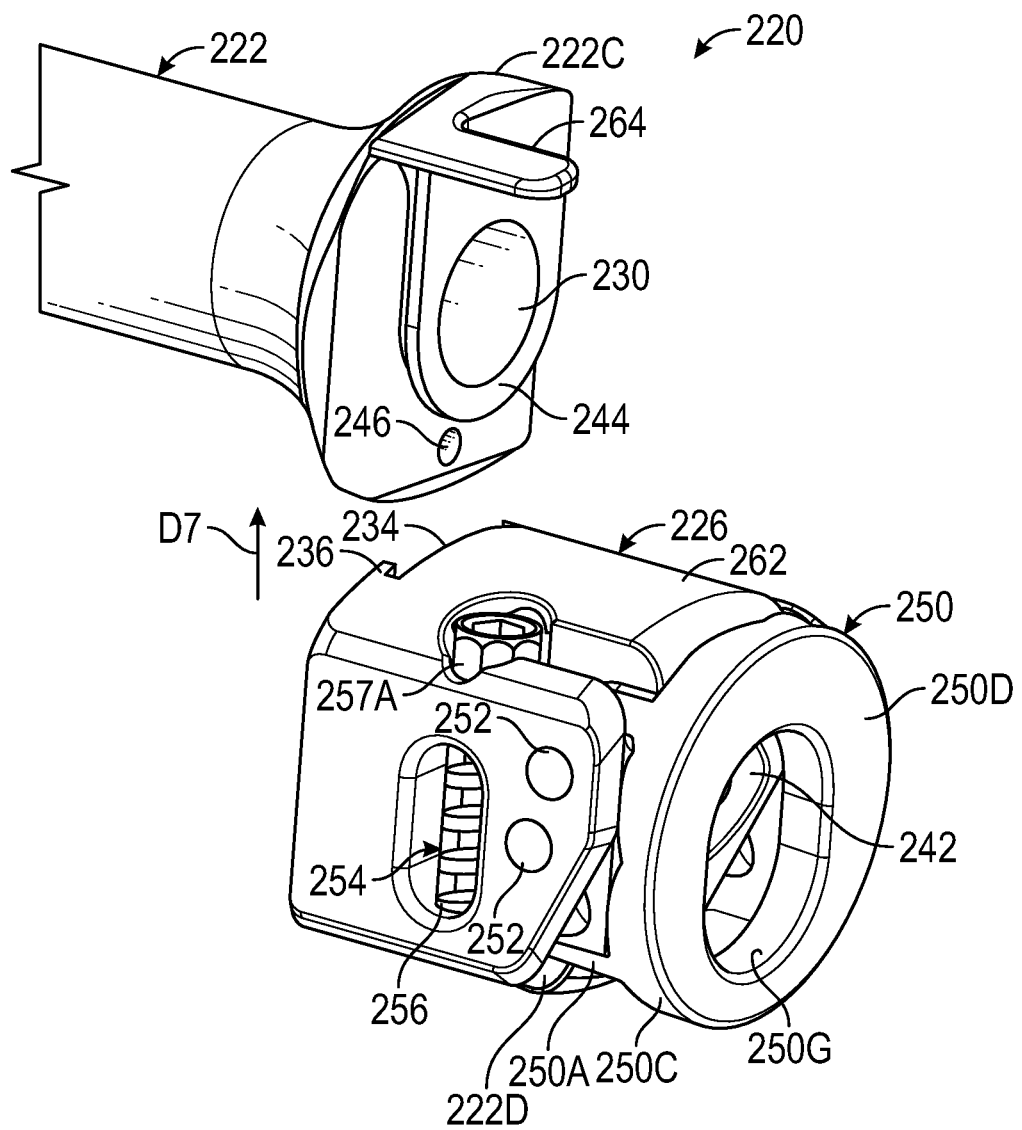
FIG. 30 illustrates the head assembly of FIG. 29 in an uninstalled position.
Figure 31:
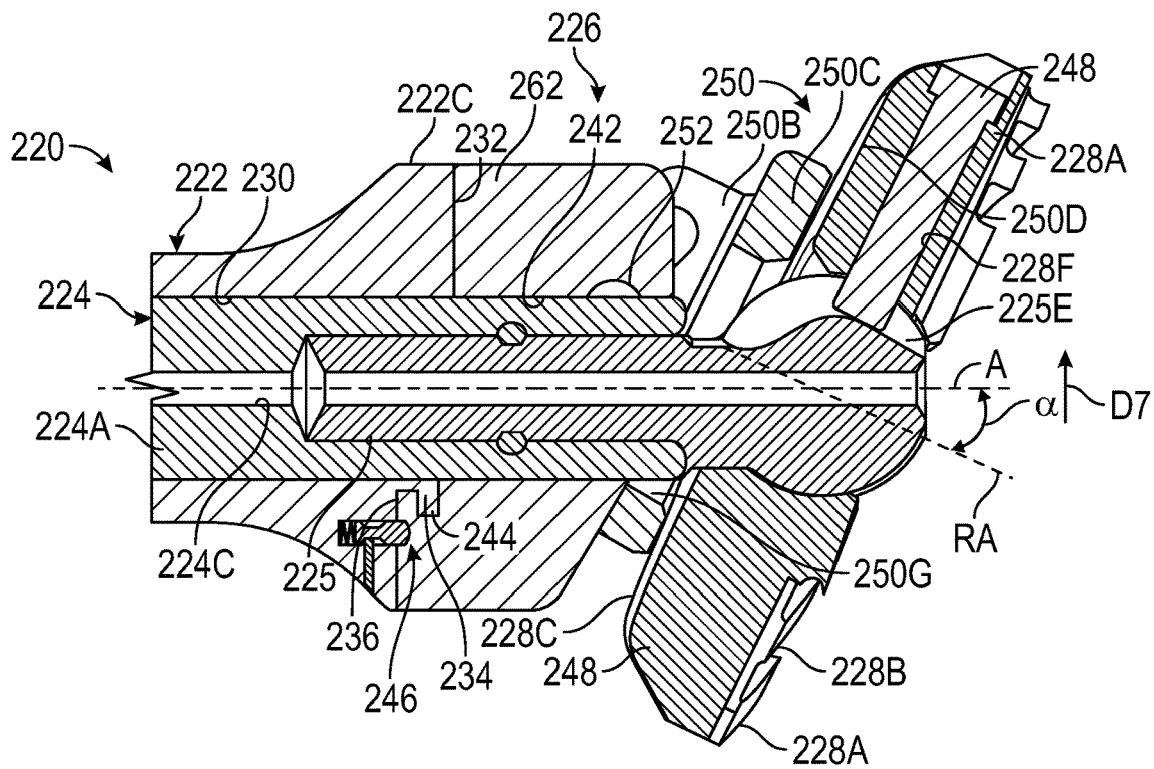
FIG. 31 illustrates a sectional view of the head assembly of FIG. 29.

Referring to FIGS. 29-31, with continuing reference to FIG. 28, the head assembly 226 includes a head plate 250 pivotably attached to the support 262. The head plate 250 includes a control flange 250A and a mounting flange 250B that extend outwardly from a plate body 250C. The support 262 defines a pair of recesses 222D, 222E that are dimensioned to at least partially receive the respective flanges 250A, 250B, as illustrated in FIG. 29. The plate body 250C defines a control surface 250D and an opening 250G dimensioned to at least partially receive a reaming carrier 225. The head plate 250 can be secured to the support 262 and arranged to orient the reaming head 228 in the manner disclosed for head plate 150 and reaming head 128 in the embodiment of FIGS. 19-25. The flanges 250A, 250B are pivotably attached to the support 262 utilizing one or more support pins or fasteners 252.

The head assembly 226 includes a drive member 254 (FIGS. 29-30) operable to adjust an orientation of the control surface 250D of the head plate 250 relative to the longitudinal axis A. In the illustrated embodiment of FIGS. 28-30, the drive member includes a worm drive 256 that is at least partially received in the support 262.

The support 262 is releasably secured to a distal end portion 222C of the housing 222 along an interface 232 (FIG. 31). The support 262 can be releasably secured to the housing 222 in a similar manner as the control block 26 and housing 22 of FIGS. 4 and 5.

In the illustrative embodiment of FIGS. 30 and 31, the support 262 is dimensioned to slidably engage the distal end portion 222C of the housing 222 along the interface 232 to limit axial movement of the support 262 relative to the longitudinal axis A. The support 262 defines a retention slot 234 that extends inwardly from a retention flange 236. The flange 236 can have a generally C-shaped geometry. The support 262 defines a through bore 242 extending inwardly from the flange 236. The through bore 242 is dimensioned to at least partially receive a reaming carrier 225, as illustrated in FIG. 31.

The distal end portion 222C of the housing 222 includes a mounting flange 244. Passageway 230 extends inwardly from the mounting flange 244. The mounting flange 244 and the retention slot 234 have a complementary geometry and cooperate to define the interface 232. The retention slot 234 is dimensioned to slidably receive the mounting flange 244 along the interface 232 to limit axial movement of the support 262 relative to the longitudinal axis A. The mounting flange 244 is dimensioned such that the support 262 translates through a projection of the longitudinal axis A in response to moving the support 262 in a direction D7 (FIGS. 30 and 31) along the interface 232. Of course, an opposite configuration is also contemplated in which the support 262 is at least partially received in the housing 222.

Referring to FIGS. 29 and 30, the reaming assembly 220 includes an access flange 264 that extends outwardly from the distal end portion 222C of the housing 222. The access flange 264 is dimensioned to at least partially conceal or block access to a head portion 257A of the drive member 254 when the support 262 is secured to the housing 222. The reaming assembly 220 can include at least one locking member 246 (FIG. 30) operable to oppose movement of the support 262 relative to the distal end portion 222C of the housing 222 along the interface 232. The access flange 264 can serve to preclude or otherwise limit adjustment of the orientation of the reaming head 228 subsequent to securing the support 262 to the housing 222.

Figure 32:
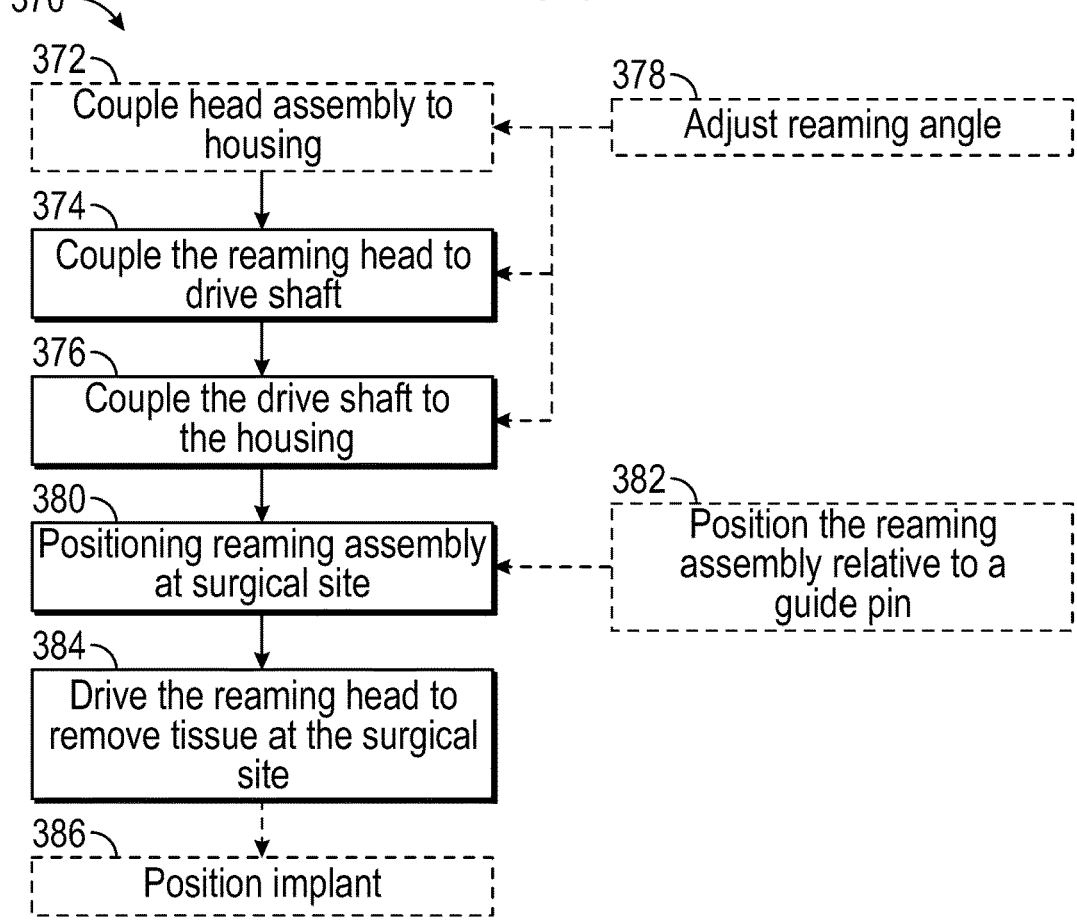
FIG. 32 illustrates an exemplary method for preparing a surgical site.

An exemplary method of use will now be described. Referring to FIG. 32, an exemplary method in a flowchart 370 for preparing a surgical site is shown. Reference is made to the reaming assembly 220 of FIGS. 28-31 for illustrative purposes. In should be appreciated that one or more of the steps of method 370 may be performed with the reaming assemblies 20 and/or 120. The method 370 can be utilized to forming a recess or cut at a surgical site, such as a bone hole in an articulating surface of a glenoid. The bone may be removed from a defect in the articulating surface. Fewer or additional steps than are recited below could be performed within the scope of this disclosure, and the recited order of steps is not intended to limit this disclosure.

At step 372, the head assembly 226 is coupled to the housing 222. Step 372 can include moving the head assembly 226 in the direction D7 (FIGS. 30 and 31) toward the longitudinal axis A and slidably engaging the head assembly 226 along the interface 232 to secure the head assembly 226 to the housing 222, as illustrated in FIG. 31. Slidably engaging the head assembly 226 along the interface 232 can include moving the head assembly 226 through a projection of the longitudinal axis A. At step 374, the reaming head 228 is pivotably coupled to the reaming carrier 225.

At step 376, the drive shaft 224 is coupled to the housing 222. Step 376 can include inserting the shaft portion 224A of the drive shaft 224 into the passageway 230 and inserting the reaming carrier 225 into and through the bore 250G of the head plate 250, as illustrated in FIG. 31. The shaft portion 224A of the drive shaft 224 and the reaming carrier 225 are fixedly attached or otherwise secured to each other in the passageway 230 to operably couple the drive shaft 224 and the reaming head 228. The reaming carrier 225 can be pivotably coupled to the reaming head 228 along the longitudinal axis A such that the control surface 250D faces away from the distal end portion 222C of the housing 222 at a non-orthogonal angle relative to the longitudinal axis A, as illustrated in FIG. 31.

At step 378, a reaming angle α (FIG. 31) of the reaming head 228 can be adjusted utilizing any of the techniques disclosed herein. Various techniques can be utilized to determine the reaming angle α parameter. For example, a defect in the glenoid can be characterized by the Walch Classification. The surgeon can measure bone loss utilizing imaging of the surgical site, such a radiogram or computed tomography technique, or can approximate a profile of the defect utilizing one or more sizers and/or measuring devices placed against the bone surface. The reaming angle α parameter can be selected to approximate the profile of the defect.

In embodiments, step 378 includes adjusting the reaming angle α in response to rotating or otherwise moving the drive member 254 to cause the head plate 250 to pivot or tilt relative to the longitudinal axis A. In the embodiment of FIGS. 24A-24C, the worm drive 156 of the drive member 154 is rotated about the drive axis DA (see FIGS. 24A-24C) to cause the engagement teeth 158 to translate along the worm drive 156. The reaming angle α (FIGS. 22 and 24B-24C) can be set prior to and/or after coupling the head assembly 226 to the housing 222.

Figure 33:
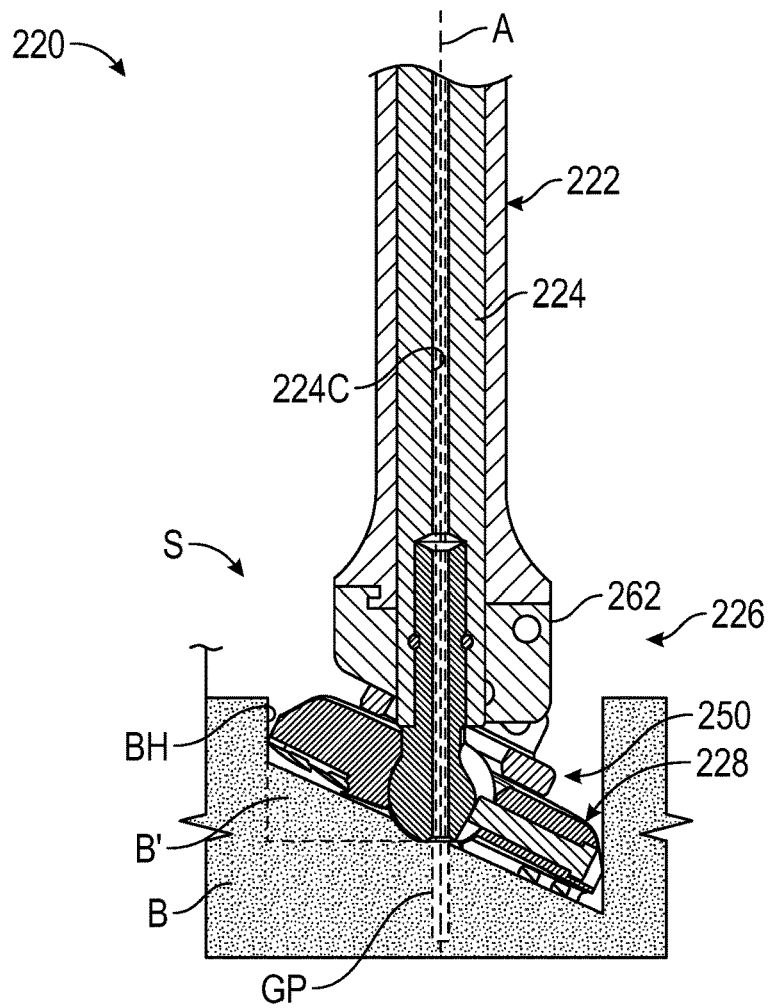
FIG. 33 schematically illustrates a reaming assembly positioned at a surgical site.

Referring to FIG. 33, with continuing reference to FIG. 32, at step 380 the reaming assembly 220 is positioned at a surgical site S. The locking member 246 is omitted for illustrative purposes. In an embodiment, the surgical site S is a glenoid of a shoulder joint. However, the method could be performed to repair defects in various other tissue within the scope of this disclosure. In other words, this disclosure is in no way limited to repairing bone defects of the glenoid.

Step 380 can include positioning the reaming assembly 220 relative to a guide pin GP (shown in dashed lines for illustrative purposes) at step 382. The guide pin GP may be positioned at least partially in the inner bore 224C of the drive shaft 224.

Figure 34:
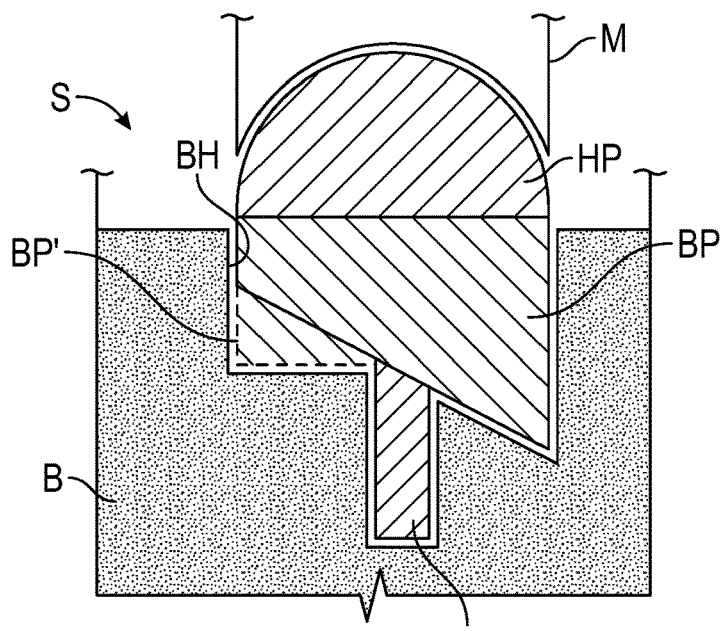
FIG. 34 illustrates an implant positioned at the surgical site of FIG. 33.

At step 384, the surgical site S may be prepared for receiving an implant or bone plate BP (FIG. 34). The reaming head 228 is driven by the drive shaft 224 to form at least one recess or bone hole BH by removing tissue such as bone B at the surgical site S. The hole BH may be formed to remove tissue from a defect in the bone B. Step 384 includes rotating the reaming head 228 along the control surface 250D to remove bone B in response to rotating the drive shaft 224. The reaming head 228 forms an angled cut in the bone B. Step 384 can include rotating the reaming head 228 about the guide pin GP to remove the bone B. A portion B' (shown in dashed lines) of the bone B can be removed prior to or after reaming the bone B with the reaming assembly 220.

Referring to FIG. 34, with continuing reference to FIGS. 32-33, at step 386 the bone plate BP can be positioned in the bone hole BH. A backside of the bone plate BP includes an augmented portion having a generally wedge-shaped geometry. The bone plate BP can include a portion BP' positioned in the area in which the portion B' of the bone B is removed such that the augmented portion extends only partially between opposed sides of the bone plate BP. The bone plate BP can include an anchoring member BP-M to secure the bone plate BP at the surgical site S.

A head portion or glenosphere HP can be secured to the bone plate BP to provide an articulating surface for mating with an opposed articulating member M. The articulating member M can be an implant secured to the humerus, for example. In other embodiments, the bone plate BP provides the articulating surface.

The novel devices and methods of this disclosure provide versatility in dimensioning or shaping a recess at a surgical site. The disclosed reaming assemblies can be utilized to form an angled cut at the surgical site to more closely approximate a contour of a bone surface, such as a bone void, which can lead to improved healing at the surgical site.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A reaming assembly for preparation of a surgical site, comprising:
    a housing defining a passageway that extends along a longitudinal axis;
    a rotatable drive shaft at least partially received in the passageway;
    a reaming head pivotably coupled to a reaming carrier, the reaming carrier operably coupled to the drive shaft, the reaming head including a plurality of teeth rotatable about a reaming axis;
    at least one control block including a block body having a control surface and a through bore extending from the control surface along a block axis, wherein the at least one control block is dimensioned to slidably engage the housing along an interface to secure the at least one control block such that the control surface faces away from a distal end portion of the housing, the through bore is dimensioned to at least partially receive the reaming carrier, the control surface is non-orthogonal relative to the block axis such that a reaming angle is defined between the longitudinal axis and the reaming axis, and the reaming head is rotatable along the control surface to remove bone;
    wherein the at least one control block is dimensioned to space apart the reaming head and the housing in an installed position;
    wherein the at least one control block includes a mounting flange extending outwardly from the block body, and the distal end portion of the housing defines a slot dimensioned to slidably receive the mounting flange along the interface to limit axial movement of the at least one control block relative to the longitudinal axis; and
    wherein the mounting flange is dimensioned such that the block body translates through a projection of the longitudinal axis in response to moving the mounting flange along the interface.

2. The assembly as recited in claim 1, wherein the at least one control block includes first and second control blocks dimensioned such that the reaming angle of the first control block differs from the reaming angle of the second control block.

3. The assembly as recited in claim 1, wherein the drive shaft is a cannulated drive shaft including an inner bore dimensioned to receive a guide pin.

4. The assembly as recited in claim 1, further comprising at least one locking member including an engagement pin moveable between a retracted position and an extended position, and wherein the engagement pin extends across the interface to oppose movement of the at least one control block relative to the housing along the interface in the extended position.

5. A reaming assembly for preparation of a surgical site, comprising:
    a housing defining a passageway that extends along a longitudinal axis;
    a rotatable drive shaft at least partially received in the passageway;
    a reaming head operably coupled to the drive shaft, the reaming head including a plurality of teeth rotatable about a reaming axis;
    a head assembly coupled to the housing, the head assembly including a head plate and a drive member, the head plate having a control flange and a plate body having a control surface, the control flange extending from the plate body and engaging the drive member, wherein the reaming head is rotatable along the control surface to remove bone, and the control flange adjusts an orientation of the control surface relative to the longitudinal axis in response to rotation of the drive member;
    wherein the reaming head is pivotably attached to a reaming carrier, and the reaming carrier interconnects the reaming head and the drive shaft; and
    wherein the drive shaft is coupled to the reaming carrier at a position within the passageway, the drive shaft extends outwardly from a proximal end portion of the housing, and the reaming carrier extends through an opening defined in the control surface.

6. The assembly as recited in claim 5, wherein the reaming carrier includes an elongated drive portion extending from a head portion, the drive portion coupled to drive shaft, the head portion pivotably attached to the reaming head, and the head portion including a plurality of protrusions dimensioned to mesh with the plurality of teeth.

7. The assembly as recited in claim 5, wherein the drive shaft is a cannulated drive shaft including an inner bore dimensioned to at least partially receive a guide pin.

8. The assembly as recited in claim 5, wherein the head plate is pivotably attached to a distal end portion of the housing.

9. The assembly as recited in claim 8, wherein the control flange defines an arcuate groove dimensioned to receive one or more support pins fixedly attached to the distal end portion of the housing.

10. A reaming assembly for preparation of a surgical site comprising:
    a housing defining a passageway that extends along a longitudinal axis;
    a rotatable drive shaft at least partially received in the passageway;
    a reaming head operably coupled to the drive shaft, the reaming head including a plurality of teeth rotatable about a reaming axis;
    a head assembly coupled to the housing, the head assembly including a head plate and a drive member, the head plate having a control flange and a plate body having a control surface, the control flange extending from the plate body and engaging the drive member, wherein the reaming head is rotatable along the control surface to remove bone, and the control flange adjusts an orientation of the control surface relative to the longitudinal axis in response to rotation of the drive member; and
    wherein the drive member comprises a worm drive that meshes with a plurality of engagement teeth along the control flange.

11. The assembly as recited in claim 10, wherein the worm drive is rotatable about a drive axis that is transverse to the longitudinal axis.

12. The assembly as recited in claim 10, wherein the reaming head is pivotably attached to a reaming carrier, the reaming carrier interconnects the reaming head and the drive shaft, the reaming carrier extends through an opening defined in the control surface, the head plate is pivotable relative to the longitudinal axis to set a reaming angle of the reaming head in response to translation of the plurality of engagement teeth along the worm drive, and the reaming carrier is straight when the head plate is positioned at the maximum angle.

13. A reaming assembly for preparation of a surgical site comprising:
- a housing defining a passageway that extends along a longitudinal axis;
- a rotatable drive shaft at least partially received in the passageway;
- a reaming head operably coupled to the drive shaft, the reaming head including a plurality of teeth rotatable about a reaming axis;
- a head assembly coupled to the housing, the head assembly including a head plate and a drive member, the head plate having a control flange and a plate body having a control surface, the control flange extending from the plate body and engaging the drive member, wherein the reaming head is rotatable along the control surface to remove bone, and the control flange adjusts an orientation of the control surface relative to the longitudinal axis in response to rotation of the drive member; and
- wherein the head assembly includes a support releasably secured to a distal end portion of the housing at an interface, and the control flange is pivotably attached to the support.

14. The assembly as recited in claim 13, wherein the drive member comprises a worm drive that meshes with a plurality of engagement teeth along the control flange, the support defines a recess that at least partially receives the control flange, and the worm drive is at least partially received in the support.

15. The assembly as recited in claim 14, wherein the worm drive extends along a worm shaft, the worm shaft includes a head portion dimensioned to engage tooling to rotate the worm shaft about a drive axis, and the distal end portion of the housing includes an access flange dimensioned to at least partially block access to the head portion when the support is secured to the housing.

16. The assembly as recited in claim 14, wherein the support slidably engages the distal end portion of the housing along the interface to limit axial movement of the support relative to the longitudinal axis.

17. The assembly as recited in claim 16, further comprising at least one locking member including an engagement pin moveable between a retracted position and an extended position, and wherein the engagement pin extends across the interface to oppose movement of the support relative to the distal end portion of the housing along the interface in the extended position.

* * * * *

UNITED STATES PATENT AND TRADEMARK OFFICE
CERTIFICATE OF CORRECTION

PATENT NO. : 11,246,604 B2
APPLICATION NO. : 16/590754
DATED : February 15, 2022
INVENTOR(S) : Alexander Emmanuel Rodriguez et al.

It is certified that error appears in the above-identified patent and that said Letters Patent is hereby corrected as shown below:

On the Title Page

Item (72) Inventors: Line 3; replace "Tyler Clevett," with --James Tyler Clevett,--

Signed and Sealed this
Twentieth Day of September, 2022

Katherine Kelly Vidal
*Director of the United States Patent and Trademark Office*